(12) United States Patent
Gill et al.

(10) Patent No.: US 6,528,653 B2
(45) Date of Patent: Mar. 4, 2003

(54) THIENOPYRROLIDINONES

(75) Inventors: Adrian Liam Gill, Wilshamstead; William Harris, Henlow, both of (GB)

(73) Assignee: Hoffmann-La Roche, Inc., Nutley, NJ (US)

( * ) Notice: Subject to any disclaimer, the term of this patent is extended or adjusted under 35 U.S.C. 154(b) by 0 days.

(21) Appl. No.: 09/891,588

(22) Filed: Jun. 26, 2001

(65) Prior Publication Data

US 2002/0028841 A1 Mar. 7, 2002

(30) Foreign Application Priority Data

Jul. 4, 2000 (GB) .............................. 0016454

(51) Int. Cl.[7] .................... C07D 233/54; C07D 231/10; A61K 31/4155
(52) U.S. Cl. .................... 548/311.4; 548/455; 548/453; 548/364.1; 514/415; 514/399
(58) Field of Search .................... 548/311.7, 364.1, 548/453, 455; 514/415, 399, 455

(56) References Cited

U.S. PATENT DOCUMENTS

| 4,797,413 A | 1/1989 | Baldwin et al. |
| 4,863,092 A | 9/1989 | Nguyen et al. |
| 6,197,804 B1 | 3/2001 | Luk et al. |
| 6,221,867 B1 | 4/2001 | Corbett et al. |

FOREIGN PATENT DOCUMENTS

| WO | WO 96/40116 | 12/1996 |
| WO | WO 97/45409 | 12/1997 |
| WO | WO 98/07695 | 2/1998 |
| WO | WO 98/24432 | 6/1998 |
| WO | WO 98/50356 | 11/1998 |
| WO | WO 99/10325 | 3/1999 |
| WO | WO 99/15500 | 4/1999 |
| WO | WO 99/21856 | 5/1999 |

OTHER PUBLICATIONS

Wensbo et al Tetrahedron vol. 51, No. 37, pp 10323–10342, 1995.*

Tetrahedron, vol. 51, No. 37, 1995, pp. 10323–10342.

* cited by examiner

*Primary Examiner*—Floyd D. Higel
*Assistant Examiner*—Komal Saeed
(74) *Attorney, Agent, or Firm*—George W. Johnston; Patricia S. Rocha-Tramaloni

(57) ABSTRACT

The invention is directed to substituted thieno[2,3-b] pyrrolidin-5-ones. The compounds are useful as inhibitors of cellular production of tumor necrosis factor (TNF-α) and as antiproliferative agents. These compounds are useful in the treatment or control of neuro-degenerative diseases, cardio-vascular diseases, cancer or inflammatory diseases.

29 Claims, No Drawings

THIENOPYRROLIDINONES

FIELD OF THE INVENTION

The present invention relates to bicyclic sulfur containing heteroaryls. More particularly, the invention is directed to substituted thieno[2,3-b]pyrrolidin-5-one derivatives, a process for their manufacture and pharmaceutical preparations containing them. This invention is further directed to intermediates useful in the preparation of the foregoing compounds and to processes for the preparation of such compounds. These novel thienopyrrolidinones inhibit or modulate the production of tumour necrosis factor (TNF-α) from cells. Compounds of the invention also inhibit the proliferation of cells. These compounds and their pharmaceutically acceptable salts are useful as anti-inflammatory agents, particularly useful in the treatment of rheumatoid arthritis, neuro-degenerative diseases such as Alzheimer's, cardiovascular diseases and in cancer therapy. The invention is also directed to pharmaceutical compositions containing these compounds.

SUMMARY OF THE INVENTION

The present invention relates to thienopyrrolidinones of the formula

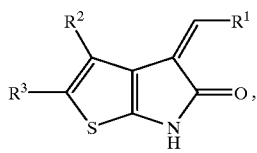

I wherein $R^1$, $R^2$ and $R^3$ are as defined below.

These compounds inhibit or modulate TNF-α from cells and also inhibit cell proliferation. These compounds are useful as anti-inflammatory agents, particularly in the treatment of rheumatoid arthritis.

DETAILED DESCRIPTION OF THE INVENTION

The present invention relates to thienopyrrolidinones of the formula

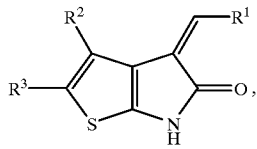

I and pharmaceutically acceptable salts thereof,
wherein
$R^1$ represents a 5- or 6-membered monocyclic aromatic ring containing one or more, preferably 1–4, hetero atoms independently selected from N, S and O, the remaining atoms being carbon, said 5- or 6-membered aromatic ring optionally being fused to a benzene ring, said 5- or 6-membered monocyclic aromatic ring and said benzene ring each being independently optionally substituted with one or more substituents selected from the group consisting of lower alkl, lower alkoxy, optionally substituted aryl, optionally substituted aryl-lower alky, optionally substituted aryl-lower alkoxy, halogen, haloalkyl, nitro, hydroxy, cyano, —C(O)$R^7$, —(CH$_2$)$_n$CO$_2$$R^8$, and —(CH$_2$)$_n$CONR$^7$$R^8$;

$R^7$ is selected from the group consisting of hydrogen, cycloalkyl, optionally substituted aryl, optionally substituted heteroaryl, heterocyclyl, and lower alkyl that optionally may be mono substituted by cycloalkyl, optionally substituted aryl or heterocyclyl;

$R^8$ is selected from the group consisting of hydrogen, cycloalkyl, heterocyclyl and lower alkyl that optionally may be mono substituted by cycloalkyl, optionally substituted aryl, hydroxy, lower alkoxy, optionally substituted heteroaryl, heterocyclyl or hydroxy-loweralkoxy, or, when $R^7$ and $R^8$ are both attached to nitrogen, $R^7$ and $R^8$ together with the nitrogen atom to which they are attached represent a 5- or 6-membered heterocycle optionally containing an additional heteroatom selected from N, S and O and optionally being substituted by lower alkyl, lower alkoxy or hydroxy-lower alkyl;

n is 0–3;

$R^2$ is H;

$R^3$ is selected from the group consisting of hydrogen, —COR$^4$, —CONR$^4$R$^5$, —CONHOR$^6$, cyano, halogen, —CO$_2$R$^5$, —SO$_2$NR$^4$R$^5$, —OR$^4$, lower alkyl optionally substituted independently by cycloalkyl, optionally substituted aryl, optionally substituted heteroaryl, heterocyclyl, hydroxy, —CONR$^4$R$^5$, or —CO$_2$R$^5$, and lower alkenyl optionally substituted independently by cycloalkyl, optionally substituted aryl, optionally substituted heteroaryl, heterocyclyl, hydroxy, —CONR$^4$R$^5$ or —CO$_2$R$^5$;

$R^4$ is selected from the group consisting of hydrogen, cycloalkyl, optionally substituted aryl, optionally substituted heteroaryl, heterocyclyl, and lower alkyl that may be optionally mono substituted by cycloalkyl, optionally substituted aryl or heterocyclyl;

$R^5$ is selected from the group consisting of hydrogen, cycloalkyl, optionally substituted aryl, optionally substituted heteroaryl, heterocyclyl, and lower alkyl optionally substituted independently by —CONH$_2$, cycloalkyl, optionally substituted aryl, optionally substituted aryloxy, hydroxy, lower alkoxy, optionally substituted heteroaryl, heterocyclyl, hydroxy-loweralkoxy or —NR'R" wherein R' is hydrogen or lower alkyl optionally substituted by optionally substituted aryl and R" is —COCH$_3$, lower alkyl or optionally substituted aryl;

or alternatively, when $R^4$ and $R^5$ are both attached to nitrogen, $R^4$ and $R^5$ together with the nitrogen atom to which they are attached represent a 5- or 6-membered heterocycle optionally containing an additional heteroatom selected from N, S and O and optionally being independently substituted at one or more carbon and/or N-atoms by lower alkyl, lower alkoxy or hydroxy-lower alkyl;

$R^6$ represents hydrogen or heterocyclyl.

The compounds of the present invention, depending on the nature of the substituents, may possess one or more asymmetric carbon atoms. The invention include all such forms (e.g., enantiomers, diastereoisomers) and to mixtures thereof, including enantiomeric mixtures (racemates), diastereoisomeric mixtures and mixtures of both such mixtures.

As used herein, the term "lower alkyl" means a saturated straight-chain or branched-chain hydrocarbon containing from 1 to 7, preferably from 1 to 4, carbon atoms, such as methyl, ethyl, n-propyl, isopropyl, n-butyl, sec.butyl, tert.butyl, n-pentyl, n-hexyl, n-heptyl and the like.

The term "lower alkoxy" means a lower alkyl group as defined earlier which is bonded via an oxygen atom, with examples of lower alkoxy groups being methoxy, ethoxy, n-propoxy, isopropoxy, n-butoxy, sec.butoxy, tert-butoxy, n-pentoxy and the like.

The term "lower alkenyl" means a lower alkyl group as defined earlier which contains one double bond of either E or Z stereochemistries, for example ethenyl, prop-2-enyl, but-2-enyl, 2-ethenyl-butyl and the like.

The term "cycloalkyl" means a saturated cyclic hydrocarbon group of 3 to 8 carbon atoms, for example cyclopropyl, cyclobutyl, cyclopentyl, cyclohexyl, cycloheptyl or cyclooctyl.

The term "benz-fused" means fused to a benzene ring or a substituted benzene ring.

The term "optionally substituted aryl" means a phenyl or an optionally partly saturated naphthyl group which is unsubstituted or optionally substituted with one or more, preferably one or two, substituents selected from halogen, lower alkoxy, haloalkyl, hydroxy, —COOR' (wherein R' is H, lower alkyl), nitro, amino, sulfamoyl, phenyl or lower alkyl optionally mono substituted by lower alkoxy or hydroxy, particularly by halogen, lower alkyl, lower alkoxy, trifluoromethyl, hydroxy, nitro, amino or sulfamoyl. The term "partly saturated naphthyl" means a naphthyl group, to which one or two $H_2$ molecules were added. An example of a partially saturated naphthyl group is 1,2,3,4-tetrahydro-1-naphthyl.

The term "aryloxy" means a group $R^a$—O—, wherein $R^a$ is optionally substituted aryl as defined above.

The term "optionally substituted heteroaryl" means an aromatic group of 5- or 6 ring atoms containing one or more, preferably 1–4, hetero atoms independently selected from N, S and O, the remaining ring atoms being C, and which aromatic group is optionally fused with a benzene ring (i.e. "benz-fused"). The heteroaryl is optionally substituted independently at one or more, preferably one or two, ring atoms by halogen, lower alkyl optionally substituted by lower alkoxy or hydroxy, lower alkoxy, haloalkyl, hydroxy, —COOR' (wherein R' is H, lower alkyl), nitro, amino, sulfamoyl or optionally substituted aryl; particularly by halogen, lower alkyl, lower alkoxy, trifluoromethyl, hydroxy, nitro, amino or sulfamoyl. Examples of heteroaryl groups are pyrrolyl, pyrazolyl, thienyl, furanyl, pyridyl, pyrimidinyl, quinolyl, indolyl, benzofuranyl, imidazolyl, 1,2,3-triazolyl, 1,2,4-triazolyl, tetrazolyl and, if benz-fused, indolyl, benzofuranyl, or benzimidazolyl. Examples of substituted heteroaryl groups are 5-methyl-3H-imidazol-4-yl, 1-methyl-2-pyrrolyl, 3-methoxy-1H-pyrrol-2-yl, 3-phenyl-1H-pyrazol-4-yl, 3-(4-methoxyphenyl)-1H-pyrazol-4-yl, 3-methyl-1H-pyrazol-4-yl, 5-(2-nitro-phenyl)-2H-pyrazol-3-yl, 2-ethoxycarbonyl-3-(2-ethoxycarbonyl-ethyl)-4-ethoxycarbonylmethyl-pyrrol-5-yl or 2-ethoxycarbonyl-3,4-dimethyl-pyrrol-5-yl and, if benz-fused, 5-methoxy-1H-indol-3-yl, 6-methyl-1H-indol-2-yl, 6-chloro-1H-benzimidazol-2-yl, 5-chloro-1H-benzimidazol-2-yl, 6-methoxy-1H-benzimidazol-2-yl, 1H-benzimidazol-2-yl or 6-chloro-1H-benzimidazol-2-yl.

The term "heterocyclyl" or "heterocycle" means, if not otherwise specifically defined, a saturated, or partially unsaturated, cyclic group of 3- to 7, preferably 5-or 6, ring atoms in which one or more, preferably one, two or three, ring atoms are hetero atoms/groups selected from N, S, $SO_2$ and O, the remaining being C, which is linked via a carbon or nitrogen ring atom. The term "partially unsaturated cyclic group" means a cyclic group, from whose saturated form one or two $H_2$ molecules were removed. Examples of heterocyclyl groups are azirdinyl, pyrrolidinyl, tetrahydro-furanyl, tetrahydro-thienyl, tetrahydro-pyranyl, piperidinyl, piperazinyl, morpholinyl or tetrahydro-1,1-dioxo-3-thienyl.

The term "halogen" used alone or in combination as in "haloalkyl", means fluorine, chlorine, bromine or iodine.

The term "haloalkyl" means a lower alkyl group wherein one or more, preferably one or two, hydrogens are replaced by one or more halogen atoms, for example —$CH_2Cl$, —$CF_3$, —$CH_2CCl_3$, —$CH_2CF_3$.

The term "hydroxy-lower alkyl" means a lower alkyl group as defined earlier wherein a hydrogen atom is replaced by a hydroxy group. Examples of such groups are hydroxymethyl, 3-hydroxypropyl, 2-hydroxyethyl, 2-hydroxy-1,1-dimethyl-ethyl or 5-hydroxy-pentyl.

The term "hydroxy-lower alkoxy-" means a lower alkoxy group as defined before wherein a hydrogen has been replaced by hydroxy. An example of such a group is 2-(2-hydroxy-ethoxy)ethyl.

The compounds of formula I which are acidic form pharmaceutically acceptable salts with bases such as alkali metal hydroxides (e.g. sodium hydroxide and potassium hydroxide), alkaline earth metal hydroxides (e.g. calcium hydroxide and magnesium hydroxide), ammonium hydroxide and the like. The compounds of formula I which are basic form pharmaceutically acceptable salts with inorganic as well as organic acids. Examples of inorganic acids include hydrohalic acids (e.g. hydrochloric acid and hydrobromic acid), sulfuric acid, nitric acid, phosphoric acid, etc. Organic acids include acetic acid, tartaric acid, succinic acid, fumaric acid, maleic acid, malic acid, salicylic acid, citric acid, methanesulfonic acid, p-toluenesulfonic acid, etc.

In a preferred embodiment of the compound of formula I, the monocyclic aromatic ring in $R^1$ is a 5- or 6-membered ring containing one, two, three or four heteroatoms, more preferably a 5-membered ring containing 1–4 heteroatoms. Most preferably, the monocyclic ring is selected from the group consisting of pyrrolyl, pyrazolyl, imidazolyl, 1,2,3-triazolyl, 1,2,4-triazolyl, tetrazolyl, thienyl or furanyl and, when fused to a benzene ring, benzimidazolyl or indolyl. Most preferably, the monocyclic or benz-fused ring in $R^1$ is pyrrolyl, pyrazolyl, imidazolyl, and indolyl, in particular pyrrolyl and pyrazolyl. Particularly preferred monocyclic rings within $R^1$ are 1-H-imidazol-2-yl, 1H-imidazol-4-yl, 2-pyrrolyl and 1H-pyrazol-4-yl, and, if benz-fused, 1-H-indol-3-yl or 1H-indol-2-yl, preferably pyrrol-2-yl and 1H-pyrazol-4-yl.

Preferably, the monocyclic and benz-fused rings of $R^1$ are each independently unsubstituted or are substituted independently at one or more, preferably one or two, positions with lower alkyl, lower alkoxy, optionally substituted aryl or $(CH_2)_nCO_2R^8$ wherein n and $R^8$ are as defined above.

When $R^1$ is substituted by —$(CH_2)_nCO_2R^8$, n is preferably 0–2 and $R^8$ is preferably lower alkyl, most preferably ethyl.

Most preferably, the monocyclic or benz-fused rings in $R^1$ are each independently substituted by lower alkyl, most preferably methyl; lower alkoxy, most preferably methoxy; optionally substituted aryl, most preferably phenyl, 2-nitrophenyl or 4-methoxyphenyl; and carbethoxy, carbethoxymethyl or carbethoxyethyl.

Particularly preferred $R^1$ groups are 1-H-imidazol-2-yl, 1H-imidazol-4-yl, 5-methyl-3H-imidazol-4-yl, 1-H-indol-3-yl, 5-methoxy-1H-indol-3-yl, 1H-indol-2-yl, 6-methyl-1H-indol-2-yl, 2-pyrrolyl, 1-methyl-2-pyrrolyl, 3-methoxy-1H- pyrrol-2-yl, 1H-pyrazol-4-yl, 3-phenyl-1H-pyrazol-4-yl, 3-(4-methoxyphenyl)-1H-pyrazol-4-yl, and 3-methyl-1H-pyrazol-4-yl, 5-(2-nitro-phenyl)-2H-pyrazol-3-yl, 2-ethoxycarbonyl-3-(2-ethoxycarbonyl-ethyl)-4-ethoxycarbonylmethyl-pyrrol-5-yl or 2-ethoxycarbonyl-3,4-dimethyl-pyrrol-5-yl. Of these groups, 2-pyrrolyl and 1H-pyrazol-4-yl are most preferred.

Preferred $R^3$ groups include hydrogen, lower alkyl optionally substituted by hydroxy, —$COR^4$, —$CONR^4R^5$, —$CONHOR^6$, cyano, —$CO_2R^5$, —$SO_2NR^4R^5$ or lower alkenyl optionally substituted by —$CO_2R^5$. Most preferably $R^3$ is hydrogen, —$CONR^4R^5$, —$CONHOR^6$, —$CO_2R^5$ or cyano.

When $R^3$ is —$CONR^4R^5$ or —$SO_2NR^4R^5$, $R^4$ is preferably hydrogen or lower alkyl, preferably hydrogen. The preferred lower alkyl group is methyl.

Preferred $R^5$ groups are hydrogen, cycloalkyl (e.g. cyclooctyl), optionally substituted aryl (e.g. phenyl, 1,2,3,4-tetrahydro-1-naphthyl), heterocyclyl (e.g. tetrahydro-1,1-dioxo-3-thienyl), lower alkyl (e.g. methyl, propyl, 2,2-dimethyl-1-methyl-propyl, 2-methyl-propyl) optionally substituted independently by one or more of —$CONH_2$ (e.g. 2-carbamoyl-ethyl), optionally substituted aryl (e.g. benzyl, 2-phenyl-butyl, 4-sulfamoylbenzyl), optionally substituted aryloxy (e.g. 2-phenoxy-ethyl), hydroxy (e.g. 3-hydroxypropyl, 2-hydroxyethyl, 5-hydroxy-pentyl, 2-hydroxy-1,1-dimethyl-ethyl), lower alkoxy (e.g. 2-methoxy-ethyl), optionally substituted heteroaryl (e.g., furan-2-yl-methyl, 2-thiophen-2-yl-ethyl, 2-indol-3-yl-ethyl, pyridin-4-ylmethyl, 2-pyridin-2-yl-ethyl, pyridin-2-ylmethyl, 1H-benzimidazol-2-ylmethyl, 6-chloro-1H-benzimidazol-2-ylmethyl, 2-(5-chloro-1H-benzimidazol-2-yl)-ethyl, 6-methoxy-1H-benzimidazol-2-ylmethyl, 6-chloro-1H-benzimidazol-2-ylmethyl), heterocyclyl (e.g. tetrahydrofuran-2-yl-methyl, 3-morpholin-4-yl-propyl, 2-pyrrolidin-1-yl-ethyl), hydroxy-loweralkoxy (e.g. 2-(2-hydroxy-ethoxy)ethyl), or —NR'R" wherein R' is hydrogen or lower alkyl optionally substituted by optionally substituted aryl and R" is —$COCH_3$, lower alkyl or optionally substituted aryl (e.g. 2-(N-(3-methylphenyl))-ethylamino) ethyl or 2-acetylamino-ethyl).

Most preferably, the lower alkyl in $R^5$ is mono- or di-substituted, preferably mono-substituted, by one of the above mentioned groups. If disubstituted, the lower alkyl is preferably disubstituted by optionally substituted aryl (e.g. 1,2-diphenyl-ethyl) or by optionally substituted aryl and hydroxy-lower alkyl (e.g. 2-hydroxy-1(R)-phenylethyl).

When $R^3$ is —$CONHOR^6$, $R^6$ is preferably hydrogen.
When $R^3$ is —$COR^4$, $R^4$ is preferably lower alkyl, most preferably methyl.
When $R^3$ is —$CO_2R^5$, $R^5$ is preferably hydrogen or lower alkyl (most preferably methyl or tert-butyl).
When, $R^3$ is lower alkenyl optionally substituted by —$CO_2R^5$, $R^5$ is preferably lower alkyl, especially methyl or ethyl.

Most preferably, $R^3$ is hydrogen, cyano or —$CONH_2$.
In another preferred embodiment, when $R^4$ and $R^5$ together with the nitrogen atom to which they are attached represent a 5- or 6-membered heterocycle, the heterocycle is optionally independently substituted at one or two carbon and/or N-atoms. Such preferred heterocycles are morpholino or pyrrolidinyl. Particularly preferred substituents on said heterocycle group are methyl or hydroxymethyl. An especially preferred heterocycle is morpholino and a preferred substituted heterocycle is 2(R)-(hydroxymethyl)-1-pyrrolidinyl.

A preferred heterocyclyl substituent in $R^6$ is tetrahydropyran-2-yl.

In another preferred embodiment $R^1$ is 1-H-pyrrol-2-yl and $R^3$ is hydrogen, cyano or —$CONR^4R^5$.
Particularly preferred compounds of the invention are:

(Z)-4,6-Dihydro-4-[(2-pyrrolyl)methylene]thieno[2,3-b]pyrrol-5-one,
(Z)-4,6-Dihydro-4-[(3-methoxy-1H-pyrrol-2-yl)methylene]thieno[2,3-b]pyrrol-5-one,
(Z)-5,6-Dihydro-5-oxo-4-[(1H-pyrrol-2-yl)methylene]-4H-thieno[2,3-b]pyrrole-2-carboxamide, and
(Z)-5,6-Dihydro-5-oxo-4-[(1H-pyrrol-2-yl)methylene]-4H-thieno[2,3-b]pyrrole-2-carbonitrile.

Other preferred compounds of the invention are:

(Z)-4,6-Dihydro-4-[(3-methyl-1H-pyrazol-4-yl) methylene] thieno[2,3-b]pyrrol-5-one;
(Z)-4,6-Dihydro-4-[(3-phenyl-1H-pyrazol-4-yl)methylene] thieno[2,3-b]pyrrol-5-one; and
(Z)-4,6-Dihydro-4-[[3-(4-methoxyphenyl)-1H-pyrazol-4-yl]methylene]thieno[2,3-b]pyrrol-5-one.

The present invention is also directed to a process for the preparation of compounds of formula I. The compounds of formula I and their pharmaceutically acceptable salts may be obtained by a process comprising the steps of reacting a compound of the formula

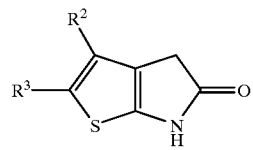

II wherein $R^2$ and $R^3$ are as above, with an aldehyde of the formula $R^1$—CHO     III wherein $R^1$ is as described above.

If desired, the compounds of formula I obtained by the above process may then be converted into a pharmaceutically acceptable salts by conventional processes known in the art of chemical synthesis.

The reaction between compounds II and III is preferably carried out in the presence of a base, such as piperidine, in a lower alkanol, such as 2-propanol, at a temperature between about 0° C. and the reflux temperature of the solvent, preferably at about 75° C.

Starting materials of formula III are either known compounds or are analogues of known compounds that can be prepared easily in a similar manner to the known compounds. Many compounds of formula III are commercially available from suppliers such as Sigma-Aldrich Company Ltd., Lancaster Synthesis Ltd. or Maybridge Chemical Company Ltd. (e.g. pyrrole-2-carboxaldehyde, Aldrich catalogue number P7, 340–4). Alternatively, starting materials of formula III may be prepared by adaptation of the methods in Vilsmeier et al., Chem. Ber., 60, 119, 1927, and Konvar et al., Tetrahedron Lett., 28, 955, 1987, for the introduction of a formyl group into appropriately substituted 5- or 6-membered monocyclic aromatic rings containing one or more hetero atoms independently selected from N, S and O. 3-substituted pyyrole-2-carboxaldehydes, such as 3-methoxypyrrole-2-carboxaldehyde (used in Examples 13, 64, 65, 66 and 67), may also be prepared by photolytic ring-contraction of the corresponding 4-substituted pyridine-N-oxides as described in Campbell, S. E. et al., J. Chem. Soc. Perkin Trans. 1, 15, 2195–2202, 1997.

Acidic compounds of formula I can be converted into pharmaceutically acceptable salts by treatment with bases using conventional processes known to those skilled in the art. Basic compounds of formula I can be converted into pharmaceutically acceptable salts by treatment with acids using conventional processes known to those skilled in the art.

Reaction schemes for manufacturing the compounds of the invention are as follows. Compounds of formula I where $R^2$ and $R^3$ are H and $R^1$ is a group as defined before, can be prepared according to scheme 1:

Compounds of formula I wherein $R^1$ is as described above, $R^2$ is H and $R^3$ is as described above, can be prepared according to scheme 2:

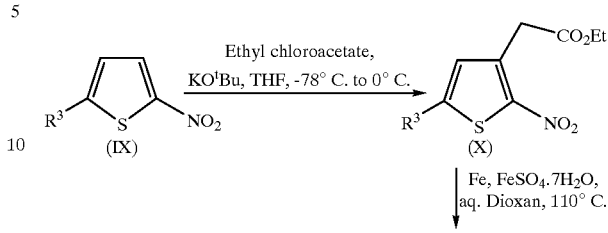

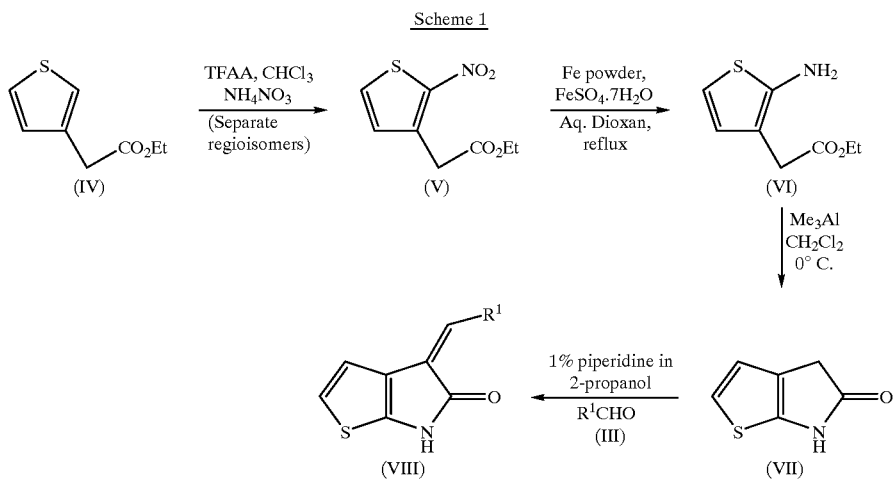

In the first step of Scheme 1, a compound of formula (IV) is reacted with a nitrating mixture, preferably with trifluoroacetic anhydride/ammonium nitrate in a halogenated aliphatic hydrocarbon, especially chloroform. This reaction may be carried out at a temperature of from about 0° C. to about 30° C.

The next step comprises reduction of the compound of formula (V) to give the amine of formula (VI). This reduction is carried out using reduced iron powder and iron sulfate heptahydrate in aqueous dioxan solvent at a temperature of from about 90° C. to about 115° C., preferably at about 110° C.

Reaction of the amine of formula (VI) with a Lewis Acid, preferably trimethylaluminium, yields the cyclised amide of formula (VII). The cyclisation is carried out in a solvent which is inert under the reaction conditions, such as tetrahydrofuran or, preferably, a halogenated aliphatic hydrocarbon, preferably dichloromethane, at a temperature of from about −78° C. to about 30° C., preferably from about 0° C. to about room temperature.

The next step comprises reacting a compound of formula (VII) with an aldehyde of formula (III) to give a compound of formula (VIII). This condensation is carried out with an organic base, preferably piperidine, in a lower alkanol such as 2-propanol, at a temperature from about 50° C. to about 100° C.

-continued

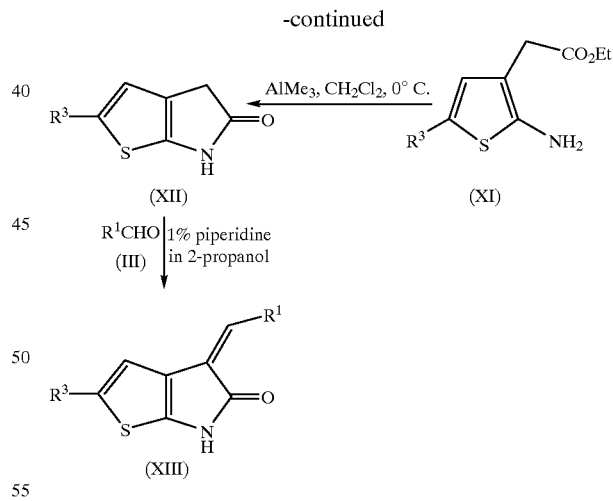

In the first step of scheme 2 above a compound of formula (IX) is reacted with ethyl chloroacetate to give a compound of formula (X). This reaction may be carried out under inert atmosphere in a solvent which is inert under the reaction conditions, preferably a cyclic ether, especially tetrahydrofuran, at a temperature of from about −78° C. to about 30° C., preferably from about −50° C. to about room temperature.

The next step comprises reduction of the compound of formula (X) to give the amine of formula (XI). This reduction is carried out using reduced iron powder and iron sulfate heptahydrate in aqueous dioxan solvent at a temperature of from about 90° C. to about 115° C., preferably at about 110° C.

Reaction of the amine of formula (XI) with a Lewis Acid, preferably trimethylaluminium, yields the cyclised amide of formula (XII). The cyclisation is carried out in a solvent which is inert under the conditions of the reaction such as tetrahydrofuran or, preferably, a halogenated aliphatic hydrocarbon, especially dichloromethane, at a temperature of from about −78° C. to about 30° C., preferably from about 0° C. to about room temperature.

The compound of formula (XII) is then reacted with an aldehyde of formula (III) to give a compound of formula (XIII). This condensation is carried out with an organic base, preferably piperidine in a lower alkanol such as 2-propanol, at a temperature of from about 50° C. to about 100° C.

Starting materials of formula (IX) are either known compounds or are analogues of known compounds that can be prepared in a similar manner to the known compounds. Thus, compounds of formula (IX) are commercially available, for example, from Sigma-Aldrich Company Ltd., Lancaster Synthesis Ltd., or Maybridge Chemical Company Ltd. (e.g. 5-nitrothiophene carboxamide, used in Example 19, Maybridge catalogue number RF 01604), or prepared by adaptation of the methods provided in Crivello et al., JOC, 1981, 46(15), 3056 for the nitration of optionally substituted thiophene rings.

It will be apparent to one skilled in the art that it may be necessary or desirable to protect reactive functional groups during synthesis. Specifically, during the conversion of a compound of formula (IX) to a compound of formula (X) in scheme 2, when $R^3$ represents formyl (i.e. $R^3$ represents $COR^4$ and $R^4$ represents hydrogen) the formyl group must be in protected form. Suitable protection is provided, for example, by using the corresponding oxime, which is prepared by reaction with hydroxylamine. Subsequent removal of the protecting group may be effected by reaction with aqueous formaldehyde using acid catalysis.

Similarly, in the conversion of a compound of formula (XI) to a compound of formula (XII) in scheme 2, when $R^3$ represents carboxylic acid (i.e. $R^3$ represents $CO_2R^5$ and $R^5$ represents hydrogen), the carboxylic acid must be protected. Suitable protection is provided, for example, by conversion to an ester, such as tert-butyl ester, which may subsequently be removed by reaction with trifluoroacetic acid.

It will also be apparent that in addition to the general syntheses detailed in schemes 1 and 2 above, these processes may in addition be combined with functional group interconversions also to yield the compounds of formula (I). For example, a carboxylic acid present in $R^1$ or $R^3$ may be converted to an amide by methods known in the art. Carboxylic acids may in turn be prepared from the corresponding carboxylic esters. In another example, a formyl group can be converted to a substituted alkenyl group by standard methods, for example by Wittig chemistry. These functional group interconversions may be carried out on compounds of formula (I) or intermediates in Schemes 1 or 2. Examples 23, 24, 66, 71, 72, 73, 74, 75 and 76 illustrate in more detail some of the functional group chemistry that may be performed.

The present invention is also directed to compounds of the formula

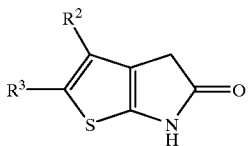

II wherein $R^2$ and $R^3$ are as defined above. These compounds are useful in the synthesis of compounds of formula (I).

The thienopyrrolidinones of the present invention are useful as inhibitors of cellular production of tumor necrosis factor (TNF-α) and as antiproliferative agents. These activities are demonstrated by using the assays described below.

The following assay may be used to demonstrate the ability of the compounds of the invention to inhibit LPS-induced TNF-α production in THP-1 cells. The assay uses a modification of the methods described in Blifield et al., Transplantation, 51:498–503 (1991).

(a) Induction of TNF Biosynthesis

THP-1 cells were suspended in serum free culture medium LGM-3 (Clonetics, Bio Whittaker, UK, Cat. No. CC-3211), at a concentration of $5 \times 10^5$ cells/ml and then plated in 96 well-plates (0.2 ml aliquots in each well). Test compounds were dissolved in DMSO and then diluted with the culture medium such that the final DMSO concentration was 1%. Twenty five μl aliquots of test solution or only medium with DMSO (control) were added to each well giving a final DMSO concentration of 0.1%. The cells were incubated for 30 min. at 37° C. LPS (Sigma Chemical Company, UK) was added to the wells at a final concentration of 2 μg/nml, and cells were incubated for an additional 4 hours. At the end of the incubation period, culture supernatants were collected and the amount of TNF-α present was determined using a commercial TNF-α ELISA assay as described below.

(b) ELISA Assay. Quantikine™ human TNF-α (R&D Systems Europe Ltd., UK) (Cat. No. DTA50 in 2000)

The assay was carried out according to the manufacturer's instructions with the following modifications. Assay plates were centrifuged at 200 g and a 200 μl sample added to each well. TNF-α standard was made up and diluted in LGM-3 culture medium. Samples in the ELISA plate were then incubated overnight at 4° C. instead of 2 hours at 37° C. TNF-α production for each condition was calculated and expressed as a percentage of DMSO control to enable $IC_{50}$ calculation.

The abbreviations used above are explained as follows:

LPS=lipopolysaccharide

TNF=tumor necrosis factor

LGM-3=lymphocyte growth medium 3

DMSO=dimethyl sulfoxide

ELISA=enzyme linked immunoabsorbent assay

Table 1 below provides $IC_{50}$ values obtained according to the above assay for selected compounds of the invention:

TABLE 1

| Example No. | Name | $IC_{50}$ (μM) |
| --- | --- | --- |
| 1 | (Z)-4,6-Dihydro-4-[(1H-pyrrol-2-yl)methylene]-thieno [2,3-b] pyrrol-5-one | 5.08 |
| 9 | (Z)-4,6-Dihydro-4-[(3-phenyl-1H-pyrazol-4-yl)methylene]thieno[2,3-b]pyrrol-5-one | 1.1 |

TABLE 1-continued

| Example No. | Name | IC$_{50}$ ($\mu$M) |
|---|---|---|
| 13 | (Z)-4,6-Dihydro-4-(3-methoxy-1H-pyrrol-2-yl)methylene] thieno [2,3-b]pyrrol-5-one | 1.59 |
| 20 | (Z)-5,6-Dihydro-5-oxo-4-[(1H-pyrrol-2-yl)methylene]-4H-thieno[2,3-b]pyrrole-2-carbonitrile | 3.69 |

The anti-proliferative activity of the compounds of the invention may be determined, for example, by use of the following assays:

The estrogen receptor negative epithelial breast carcinoma line (MDA-MB-435) can be purchased from American Type Cell Culture Collection (ATCC; Rockville, Md., USA, ATCC No. HTB-129) and grown in the medium recommended by ATCC. For analysis of the effect of the test compounds on growth of these cells, the cells are plated at 2000 cells per well in a 96-well tissue culture plate, and incubated at 37° C. with 5% $CO_2$. The next day, the test compounds are dissolved in 100% dimethyl sulfoxide (DMSO) to yield a 10 mM stock solution. Each compound is diluted with sterile medium to 1 mM in a sufficient quantity to yield a final concentration of 120 $\mu$M. The compounds are then serially diluted in medium with 1.2% DMSO. One-fourth final volume of the diluted compounds is transferred to 96-well plates. Test compounds are assayed in duplicate. DMSO is added to a row of "control cells" such that the final concentration of DMSO in each well is 0.3%. Wells to which no cells are added serve as the "blank". Wells to which no inhibitor is added serve as "no inhibitor control". The plates are returned to the incubator, and 5 days post addition of test compound, are analyzed as described below.

3(4,5-Dimethylthiazole-2-yl)-2,5-diphenyl-2H-tetrazolium bromide (thiazolyl blue; MTT) is added to each well to yield a final concentration of 1 mg/ml. The plates are then incubated at 37° C. for 3 hours. The plates are centrifuged at 1000 rpm for 5 minutes prior to aspiration of the MTT-containing medium. The MTT-containing medium is then removed and 100 $\mu$l of 100% ethanol is added to each well to dissolve the resulting formazan metabolite. To ensure complete dissolution, plates are shaken for 15 minutes at room temperature. Absorbencies are read in a microtiter plate reader (Molecular Dynamics) at a wavelength of 570 nm with a 650 nm reference. Percent inhibition is calculated by subtracting the absorbance of the blank (no cell) wells from all wells, then subtracting the division of the average of the controls from 1.00. Inhibitory concentrations (IC$_{50}$) are determined from the linear regression of a plot of the logarithm of the concentration versus the percent inhibition.

The colon carcinoma line SW480 can also be obtained from the ATCC (ATCC No. CCL-228) and tested according to the same protocol provided above with the following modification: cell line SW480 is plated at 1000 cells per well and analyzed at 4 days post addition of test compound.

The compounds of formula I are useful in the treatment or amelioration of neuro-degenerative diseases, cardiovascular diseases, cancer or as anti-inflammatory agents.

The present invention also relates to a pharmaceutical composition containing as an active ingredient at least one compound of formula I and a therapeutically inert carrier. These pharmaceutical compositions are useful in the control or prevention of neuro-degenerative diseases, cardiovascular diseases, cancer or inflammatory diseases, particularly the treatment of inflammatory diseases, associated with degenerative joint diseases such as rheumatoid arthritis and ostheoarthritis.

The compounds of formula I are inhibitors of cellular production of tumor necrosis factor (TNF-$\alpha$). TNF-$\alpha$ is a proinflammatory cytokine implicated in the pathogenesis of rheumatoid arthritis (RA). Whilst a variety of cytokines are important in the pathogenesis of RA, TNF-$\alpha$ appears to play a pivotal role (Fox, David A., Arch. Intern. Med., Vol 160(4), 437–444, 2000). The specific causative agent of the pathological process of osteoarthritis (OA) has not been identified, but episodic inflammation at the clinical stage is well documented and believed to be involved in disease progression. TNF-$\alpha$ is a predominant proinflammatory cytokine synthesized during the OA process (Martel-Pelletier, J. et al., Frontiers in Bioscience, Vol 4, d694–703, 1999; Blackburn, Warren D. Jr., American Journal of Medicine, Vol 100(no. 2 part A), 24S–30S, 1996; Sipe, J. D. et al., Mediators of Inflammation, Vol 3(4), 243–256, 1994). Abnormal expression of TNF-$\alpha$ has also been implicated in Alzheimer's disease (Mattson, Mark P. et al., Brain Research Reviews, 23, 47–61, 1997) and in the pathophysiology of heart failure (Feldman, Arthur M. et al., Journal of the American College of Cardiology, 35(3), 537–544, 2000).

The compounds of the invention are also inhibitors of cellular proliferation. Cancer is characterized by dis-regulated cellular proliferation, therefore compounds of the invention are useful in the treatment of cancer.

The pharmaceutical compositions according to the invention can be administered orally, e.g. in the form of tablets, coated tablets, dragées, hard and soft gelatin capsules, solutions, emulsions or suspensions. They can also be administered rectally, e.g. in the form of suppositories, or parenterally, e.g. in the form of injection solutions. To prepare the pharmaceutical compositions of the invention, the compounds of formula I or their pharmaceutically acceptable salts can be formulated with therapeutically inert, inorganic or organic carriers. Suitable carriers for the preparation of tablets, coated tablets, dragées and hard gelatin capsules are lactose, corn starch or derivatives thereof, talc, stearic acid or its salts. Suitable carriers for soft gelatin capsules are, for example, vegetable oils, waxes, fats, semi-solid and liquid polyols and the like. Typically, no carriers arerequired in the case of soft gelatin capsules. Suitable carriers for the manufacture of solutions and syrups are, for example, water, polyols, saccharose, invert sugar, glucose and the like. Suitable carriers for the manufacture of injection solutions are, for example, water, alcohols, polyols, glycerin, vegetable oils and the like. Natural and hardened oils, waxes, fats, semi-liquid polyols and the like are suitable carriers for the manufacture of suppositories.

The pharmaceutical compositions of the invention may also contain preservatives, stabilizers, wetting agents, emulsifiers, sweeteners, colorants, flavorants, salts for adjustment of the osmotic pressure buffers, coating agents or antioxidants.

The present invention also contemplates a process for the manufacture of the above pharmaceutical compositions.

This process comprises mixing a compound of formula I or a pharmaceutically acceptable salt thereof with a therapeutically inert carrier material to yield a galenical composition.

As mentioned earlier, the compounds of formula I and the pharmaceutically acceptable salts thereof are especially useful in the control or prevention of inflammatory diseases such as degenerative joint diseases, especially rheumatoid arthritis. They are also useful in the treatment of cardiovascular disorders, solid tumors, and neuro-degenerative diseases. The appropriate dosage of a compound of formula I can vary within wide limits and will be adjusted to the individual requirements in each patient. In general, in the case of administration to adults, a daily dosage of from about 0.1 mg/kg to about 50 mg/kg, preferably from about 0.5 mg/kg to about 5 mg/kg, is appropriate, although the upper limit may be exceeded when this is found to expedient. The daily dosage can be administered as a single dosage or in divided dosages.

EXAMPLES

The following Examples illustrate the present invention. The structure of the products was confirmed by NMR spectroscopy and mass spectroscopy.

Example 1

(Z)-4,6-Dihydro-4-[(1H-pyrrol-2yl)methylene]thieno[2,3-b]pyrrol-5-one 4,6-Dihydrothieno[2,3-b]pyrrol-5-one (30 mg, 0.22 mmol) was dissolved in a solution of 1% piperidine in 2-propanol (2 ml). Pyrrole-2-carboxaldehyde (40 mg, 0.43 mmol) was added in one portion and the mixture heated at 75° C. for 1 hour. The reaction mixture was poured into an ice/water mixture (10 ml) and the precipitated solid was collected by filtration and washed with water to give 24 mg of (Z)-4,6-dihydro-4-[(1H2-pyrrol-2-yl)methylene]thieno[2,3-b]pyrrol-5-one as a red solid. MS(ES): m/e 217 [M+H].

The starting material was prepared as follows:

i) Preparation of ethyl 2-nitrothiophene-3-acetate

Method A: Ethyl thiophene-3-acetate, (10 g, 64.1 mmol) was dissolved in chloroform (90 ml) and trifluoroacetic anhydride (40 ml) at 0° C. Ammonium nitrate (5.2 g, 64.1 mmol) was added and the reaction mixture was stirred at 0° C. for 1 hour then warmed slowly to room temperature for 2 hours. The reaction mixture was cooled in an ice-bath and diluted with dichloromethane (60 ml) and then water (50 ml). The aqueous phase was extracted with dichloromethane and the combined organic fractions were washed with saturated brine solution. The organic phase was dried over magnesium sulfate, evaporated to give a red/brown liquid which was chromatographed on silica gel using hexane/ethyl acetate (4:1) as eluent to give 8.2 g of ethyl 2-nitrothiophene-3-acetate as a red/brown viscous oil.

MS(ES): m/e 216 [M+H].

Method B: Potassium tertiary-butoxide (652 mg, 5.81 mmol) was dissolved in tetrahydrofuran (150 ml) and the solution cooled to −50° C. A solution of 2-nitrothiophene (250 mg, 1.94 mmol) (Avocado) and ethyl chloroacetate (0.22 ml, 1.94 mmol) (Aldrich) was added dropwise in dry tetrahydrofuran (4 ml) over 5 minutes. The reaction mixture was stirred at −50° C. for 1 hour then quenched with acetic acid (0.5 ml), then washed with water (20 ml). The aqueous phase was extracted with ethyl acetate and the combined organic fractions were washed with saturated brine solution. The organic phase was dried over magnesium sulfate, evaporated to dryness and the residue chromatographed on silica gel using hexane/ethyl acetate (4:1) as eluent to give 261 mg of ethyl 2-nitrothiophene-3-acetate as a red/brown viscous oil. MS(ES): mn/e 216 [M+H].

ii) Ethyl 2-nitrothiophene-3-acetate (4 g, 18.6 mmol) was dissolved in aqueous dioxan (40 ml, 4:1 dioxan/water) and treated with reduced iron powder (3.5 g, 62.7 mmol) and iron sulfate heptahydrate (400 mg, 1.44 mmol). The reaction mixture was heated at reflux for 2 hours then filtered through celite filter-aid and washed through with diethyl ether. The organic phase was washed with saturated aqueous sodium hydrogen carbonate and saturated aqueous sodium chloride. The organic phase was dried over magnesium sulfate and evaporated to a red/black liquid and then chromatographed on silica gel using hexane/ethyl acetate (3:1) as eluent to give 3.1 g of ethyl 2-aminothiophene-3-acetate. MS(ES): m/e 186 [M+H].

iii) Ethyl 2-aminothiophene-3-acetate (100 mg, 0.54 mmol) was dissolved in dry tetrahydrofuran (5 ml) and treated at −78° C. with trimethylaluminium (2M in n-heptane, 0.59 mmol). The reaction mixture was allowed to warm slowly to room temperature over 4 hours, cooled to 0° C. and quenched with saturated aqueous ammonium chloride solution. The solution was extracted with ethyl acetate and the organic phase dried over magnesium sulfate, evaporated to dryness and the residue chromatographed on silica gel using hexane/ethyl acetate (2:1) as eluent to give 45 mg of 4,6-dihydrothieno[2,3-b]pyrrol-5-one as a brown solid. MS(ES): m/e 140 [M+H].

Examples 2–18

In a manner analogous to that described in Example 1, starting with 4,6-dihydrothieno[2,3-b]pyrrol-5-one (prepared as described in Example 1) and the appropriate heterocyclic aldehyde, the compounds shown in Table 2 below were also prepared.

TABLE 2

| Example | Name | Structure | MS (ES) |
|---|---|---|---|
| 2 | (Z)-4,6-Dihydro-4-[(1-methyl-2-pyrrolyl)methylene]thieno[2,3-b]pyrrol-5-one | 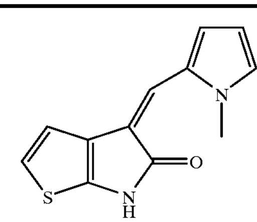 | 231 |

TABLE 2-continued

| Example | Name | Structure | MS (ES) |
| --- | --- | --- | --- |
| 3 | (Z)-4,6-Dihydro-4-[(2-thienyl)-methylene]thieno[2,3-b]pyrrol-5-one | 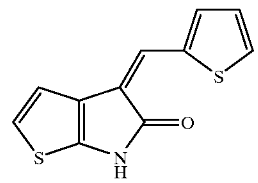 | 234 |
| 4 | (Z)-4,6-Dihydro-4-[(1H-imidazol-4-yl)methylene]thieno[2,3-b]pyrrol-5-one | 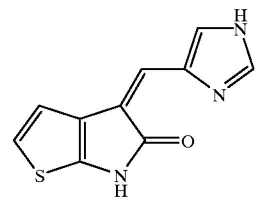 | 218 |
| 5 | (Z)-4,6-Dihydro-4-[(2-furyl)-methylene]thieno[2,3-b]pyrrol-5-one | 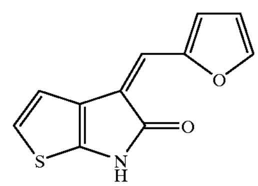 | 218 |
| 6 | (Z)-4,6-Dihydro-4-[(3-methyl-1H-pyrazol-4-yl)methylene]-thieno[2,3-b]pyrrol-5-one | 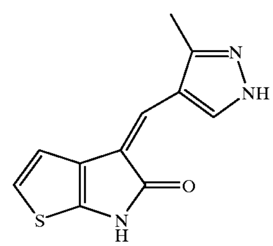 | 232 |
| 7 | (Z)-4,6-Dihydro-4-[(1H-indol-3-yl)methylene]thieno[2,3-b]pyrrol-5-one | 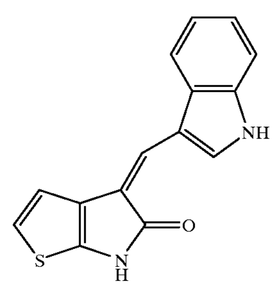 | 267 |
| 8 | (Z)-4,6-Dihydro-4-[(1H-imidazol-2-yl)methylene]thieno[2,3-b]pyrrol-5-one | 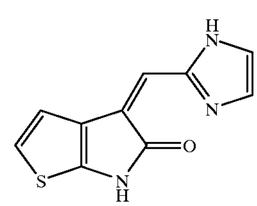 | 218 |

TABLE 2-continued

| Example | Name | Structure | MS (ES) |
|---|---|---|---|
| 9 | (Z)-4,6-Dihydro-4-[(3-phenyl-1H-pyrazol-4-yl)methylene]-thieno[2,3-b]pyrrol-5-one | 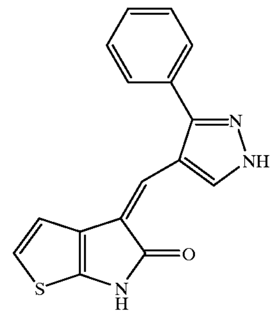 | 294 |
| 10 | (Z)-4,6-Dihydro-4-[(3-(4-methoxyphenyl)-1H-pyrazol-4-yl)methylene]thieno[2,3-b]pyrrol-5-one | 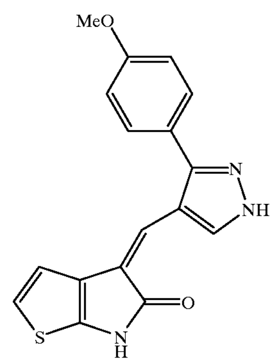 | 324 |
| 11 | (Z)-4,6-Dihydro-4-[(5-methyl-3H-imidazol-4-yl)methylene]-thieno[2,3-b]pyrrol-5-one | 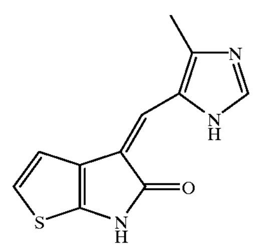 | 232 |
| 12 | (Z)-4,6-Dihydro-4-[(5-methoxy-1H-indol-3-yl)methylene]thieno-[2,3-b]pyrrol-5-one | 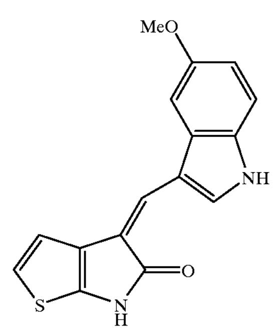 | 297 |
| 13 | (Z)-4,6-Dihydro-4-[(3-methoxy-1H-pyrrol-2-yl)methylene]-thieno[2,3-b]pyrrol-5-one | 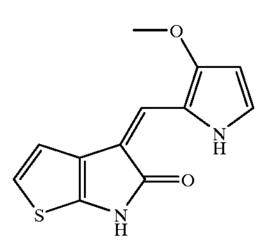 | 279 |

TABLE 2-continued

| Example | Name | Structure | MS (ES) |
|---|---|---|---|
| 14 | (Z)-4,6-Dihydro-4-[(1H-indol-2-yl)methylene]thieno[2,3-b]pyrrol-5-one | 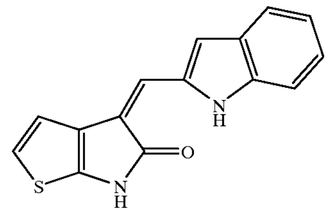 | 267 |
| 15 | (Z)-4,6-Dihydro-4-[(6-methyl-1H-indol-3-yl)methylene]thieno-[2,3-b]pyrrol-5-one | 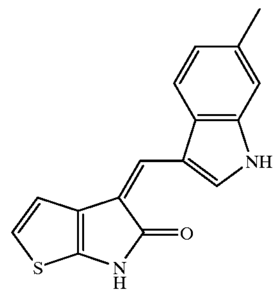 | 281 |
| 16 | (Z)-[5-(2-Nitro-phenyl)-2H-pyrazol-3-ylmethylene]-4,6-dihydro-thieno[2,3-b]pyrrol-5-one | 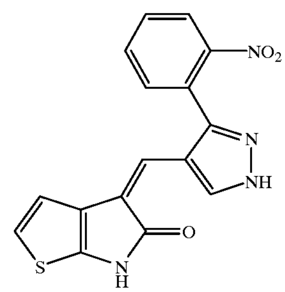 | 339 |
| 17 | 3-(2-Ethoxycarbonyl-ethyl)-4-ethoxycarbonylmethyl-5-(5-oxo-5,6-dihydro-thieno[2,3-b]pyrrol-4-ylidenemethyl)-1H-pyrrole-2-carboxylic acid ethyl ester | 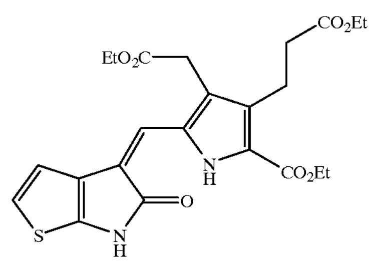 | 475 |
| 18 | 3,4-Dimethyl-5-(5-oxo-5,6-dihydro-thieno[2,3-b]pyrrol-4-ylidenemethyl)-1H-pyrrole-2-carboxylic acid ethyl ester | 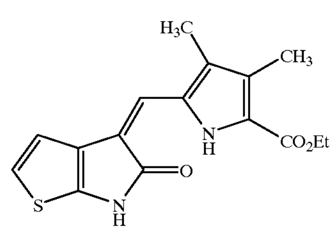 | 317 |

Example 19

(Z)-5,6-Dihydro-5-oxo-4-[(1H-pyrrol-2-yl) methylene]-4H-thieno[2,3-b]pyrrole-2-carboxamide 5,6-Dihydro-5-oxo-4H-thieno[2,3-b]pyrrole-2-carboxamide (30 mg, 0.17 mmol) was dissolved in a solution of 1% piperidine in 2-propanol (2 ml). Pyrrole-2-carboxaldehyde (16 mg, 0.18 mmol) was added in one portion and the mixture heated at 75° C. for 1 hour. The reaction mixture was poured into an ice/water mixture (10 ml) and the precipitated solid was collected by filtration and washed with water to give 15 mg of (Z)-5,6-dihydro-5-oxo-4-[(1H-pyrrol-2-yl)methylene]-4H-thieno[2,3-b]pyrrole-2-carboxamide as a yellow/brown solid.

MS(ES): m/e 260 [M+H].

The starting material was prepared as follows:

Method C i) Potassium tertiary-butoxide (1.96 g, 17.4 mmol) was dissolved in tetrahydrofuran (45 ml) and the solution cooled to −50° C. A solution of 5-nitrothiophene-2-carboxamide (1 g, 1.94 mmol) and ethyl chloroacetate (0.5 ml, 5.81 mmol) was added dropwise in dry tetrahydrofuran (12 ml) over 5 minutes. The reaction mixture was stirred at −50° C. for 16 hours then quenched with acetic acid (3 ml), then washed with water (20 ml). The aqueous phase was extracted with ethyl acetate and the combined organic fractions were washed with saturated brine solution. The organic phase was dried over magnesium sulfate, evaporated to dryness and the residue chromatographed on silica gel using hexane/ethyl acetate (4:1) as eluent to give 610 mg of ethyl 5-carbamoyl-2-nitrothiophene-3-acetate as a yellow/brown oil. MS(ES): m/e 259 [M+H].

ii) Ethyl 5-carbamoyl-2-nitrothiophene-3-acetate (600 mg, 2.33 mmol) was dissolved in aqueous dioxan (7 ml, 4:1 dioxan/water) and treated with reduced iron powder (1.55 g, 27.77 mmol) and iron sulfate heptahydrate (200 mg, 0.68 mmol). The reaction mixture was refluxed for 1 hour then filtered through celite filter-aid and washed through with ethyl acetate. The organic phase was washed with saturated sodium aqueous hydrogen carbonate and saturated aqueous sodium chloride. The organic phase was dried over magnesium sulfate and evaporated to a red/black viscous oil and then chromatographed on silica gel using hexane/ethyl acetate (1:2) as eluent to give 510 mg of ethyl 2-amino-5-carbamoylthiophene-3-acetate. MS(ES): m/e 229 [M+H].

iii) Ethyl 2-amino-5-carbamoylthiophene-3-acetate (500 mg, 2.19 mmol) was dissolved in dry dichloromethane (20 ml) and treated at 0° C. with trimethyl-aluminium (2M in heptane, 3.5 ml, 7.22 mmol). The reaction mixture was allowed to warm slowly to room temperature over 3 hours, cooled to 0° C. and quenched with saturated aqueous ammonium chloride solution. The solution was extracted with ethyl acetate, the organic phase was dried over magnesium sulfate, evaporated to dryness and the residue chromatographed on silica gel using ethyl acetate as eluent to give 210 mg of 5,6-dihydro-5-oxo-4H-thieno[2,3-b]pyrrole-2-carboxamide as a pale grey solid. MS(ES): m/e 183 [M+H].

The procedure outlined in Method C was used for the synthesis of the starting material used in Example 20 (5-nitrothiophene-2-carbonitrile), which is also commercially available. The starting materials used in Examples 21 and 22 can be prepared from the commercially available 5-nitrothiophene-2-carboxylic acid in a manner known per se. Method C was then used for preparation of the respective starting materials.

Example 20

(Z)-5,6-Dihydro-5-oxo-4-[(1H-pyrrol-2-yl)methylene]-4H-thieno[2,3-b]pyrrole-2-carbonitrile 5,6-Dihydro-5-oxo-4H-thieno[2,3-b]pyrrole-2-carbonitrile (32 mg, 0.2 mmol) was dissolved in a solution of 1% piperidine in 2-propanol (1 ml). Pyrrole-2-carboxaldehyde (37 mg, 0.39 mmol) was added in one portion and the mixture heated at 75° C. for 1 hour. The reaction mixture was poured into an ice/water mixture (6 ml) and the precipitated solid was collected by filtration and washed with water to give 10 mg of (Z)-5,6-dihydro-5-oxo-4-[(1H-pyrrol-2-yl)methylene]-4H-thieno[2,3-b]pyrrole-2-carbonitrile as a yellow solid. MS(ES): m/e 242 [M+H].

Example 21 tert-Butyl (Z)-5,6-dihydro-5-oxo-4-[(1H-pyrrol-2-yl)methylene]-4H-thieno[2,3-b]pyrrole-2-carboxylate tert-Butyl 5,6-dihydro-5-oxo-4H-thieno[2,3-b]pyrrole-2-carboxylate (32 mg, 0.2 mmol) was dissolved in a solution of 1% piperidine in 2-propanol (1 ml). Pyrrole-2-carboxaldehyde (0.39 mmol, 37 mg) was added in one portion and the mixture heated at 75° C. for 1 hour. The reaction mixture was poured into an ice/water mixture (6 ml) and the precipitated solid was collected by filtration and washed with water to give 10 mg of tert-butyl (Z)-5,6-dihydro-5-oxo-4-[(1H-pyrrol-2-yl)methylene]-4H-thieno[2,3-b]pyrrole-2-carboxylate as a yellow solid. MS(ES): m/e 317 [M+H].

Example 22

Methyl (Z)-5,6-dihydro-5-oxo-4-[(1H-pyrrol-2-yl)methylene]-4H-thieno[2,3-b]pyrrole-2-carboxylate Methyl 5,6-dihydro-5-oxo-4H-thieno[2,3-b]pyrrole-2-carboxylate (32 mg, 0.2 mmol) was dissolved in a solution of 1% piperidine in 2-propanol (1 ml). Pyrrole-2-carboxaldehyde (37 mg, 0.39 mmol) was added in one portion and the mixture heated at 75° C. for 1 hour. The reaction mixture was poured into an ice/water mixture (6 ml) and the precipitated solid was collected by filtration and washed with water to give 10 mg of methyl (Z)-5,6-dihydro-5-oxo-4-[(1H-pyrrol-2-yl)methylene]-4H-thieno[2,3-b]pyrrole-2-carboxylate as a yellow solid. MS(ES): m/e 275 [M+H].

Example 23

(Z)-5,6-Dihydro-5-oxo-4-[(1H-pyrrol-2-yl)methylene]-4H-thieno[23-b]pyrrole-2-carboxylic acid tert-Butyl (Z)-5,6-dihydro-5-oxo-4-[(1H-pyrrol-2-yl)methylene]-4H-thieno[2,3-b]pyrrole-2-carboxylate (150 mg, 0.47 mmol) was dissolved in dichloromethane (8 ml), cooled to 0° C., treated with trifluoroacetic acid (0.75 ml) and stirred for 2 hours warming to room temperature. The reaction mixture was evaporated to dryness and triturated with diethyl ether to give 70 mg of (Z)-5,6-dihydro-5-oxo-4-[(1H-pyrrol-2-yl)methylene]-4H-thieno[2,3-b]pyrrole-2-carboxylic acid as a red solid. MS(ES): m/e 260 [M+H].

Example 24

(Z)-5,6-Dihydro-5-oxo-N-propyl-4-[(1H-pyrrol-2-yl)methylene]-4H-thieno[2,3-b]pyrrole-2-carboxamide A solution of (Z)-5,6-dihydro-5-oxo-4-[(1H-pyrrol-2-yl)methylene]-4H-thieno[2,3-b]pyrrole-2-carboxylic acid (30 mg, 0.12 mmol), 1-hydroxy-benzotriazole (18 mg, 0.13 mmol), propylamine (11 μl, 0.13 mmol), 1-(3-dimethoxyaminopropyl)-3-ethylcarbodiimide hydrochloride (25 mg, 0.13 mmol) and diisopropylethylamine (23 μl, 0.13 mmol) in dimethylformamide (1 ml) was stirred at room temperature for 3 hours then diluted with ethyl acetate and washed with 2M hydrochloric acid, saturated sodium bicarbonate and water. The resulting solution was dried over magnesium sulfate and evaporated to dryness. The residue was triturated with water/isopropyl alcohol to give 14 mg of (Z)-5,6-dihydro-5-oxo-N-propyl-4-[(1H-pyrrol-2-yl)methylene]-4H-thieno[2,3-b]pyrrole-2-carboxamide as an orange solid. MS(ES): m/e 302 [M+H].

Examples 25–64

In a manner analogous to that described in Example 24, starting with (Z)-5,6-dihydro-5-oxo-4-[(1H-pyrrol-2-yl)methylene]-4H-thieno[2,3-b]pyrrole-2-carboxylic acid and the appropriate amine the compounds shown in Table 3 were also prepared.

TABLE 3

| Example | Name | Structure | MS (ES) |
|---|---|---|---|
| 25 | (Z)-5,6-Dihydro-N-(3-hydroxypropyl)-5-oxo-4-[(1H-pyrrol-2-yl)-methylene]-4H-thieno-[2,3-b]pyrrole-2-carboxamide | 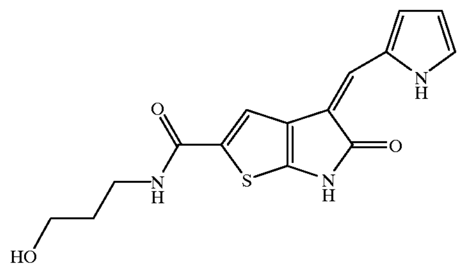 | 318 |
| 26 | (Z)-4,6-Dihydro-2-[[2(R)-(hydroxymethyl)-1-pyrrolidinyl]carbonyl]-4-[(1H-pyrrol-2-yl)-methylene]-5H-thieno-[2,3-b]pyrrol-5-one | 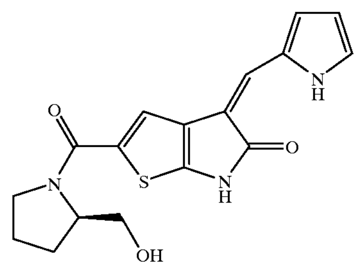 | 343 |
| 27 | (Z)-5,6-Dihydro-N-methyl-5-oxo-4-[(1H-pyrrol-2-yl)methylene]-4H-thieno[2,3-b]pyrrole-2-carboxamide | 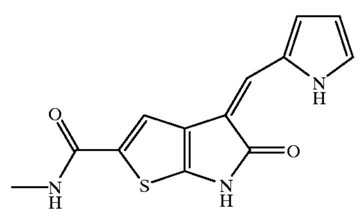 | 274 |
| 28 | (Z)-5,6-Dihydro-N,N-dimethyl-5-oxo-4-[(1H-pyrrol-2-yl)methylene]-4H-thieno[2,3-b]pyrrole-2-carboxamide | 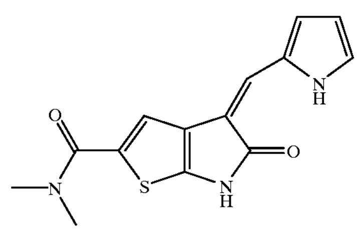 | 288 |
| 29 | (Z)-4,6-Dihydro-2-(morpholinocarbonyl)-4-[(1H-pyrrol-2-yl)-methylene]-4H-thieno-[2,3-b]pyrrole-2-carboxamide | 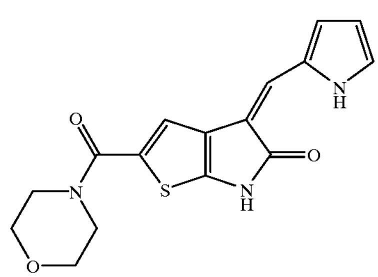 | 330 |

TABLE 3-continued

| Example | Name | Structure | MS (ES) |
|---|---|---|---|
| 30 | (Z)-N-Benzyl-5,6-dihydro-5-oxo-4-[(1H-pyrrol-2-yl)methylene]-4H-thieno[2,3-b]pyrrole-2-carboxamide | 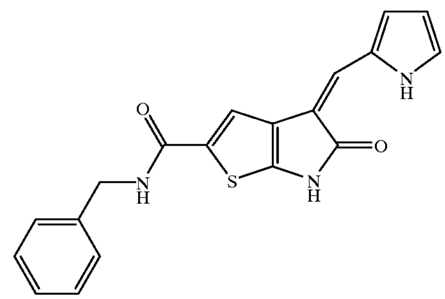 | 350 |
| 31 | (Z)-5,6-Dihydro-5-oxo-4-[(1H-pyrrol-2-yl)-methylene]-4H-thieno[2,3-b]pyrrole-2-carboxanilide | 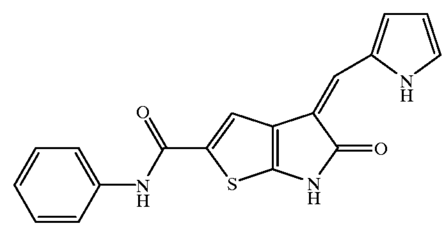 | 336 |
| 32 | (Z)-5,6-Dihydro-N-methyl-N-(2-hydroxy-ethyl)-5-oxo-4-[(1H-pyrrol-2-yl)methylene]-4H-thieno[2,3-b]pyrrole-2-carboxamide | 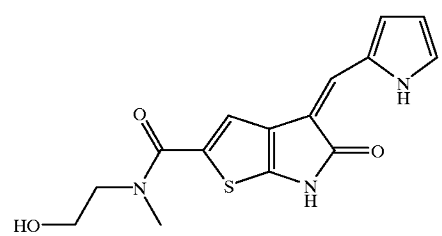 | 318 |
| 33 | (Z)-5,6-Dihydro-N-(1,2,3,4-tetrahydro-1(RS)-naphthyl)-5-oxo-4-[(1H-pyrrol-2-yl)methylene]-4H-thieno[2,3-b]pyrrole-2-carboxamide | 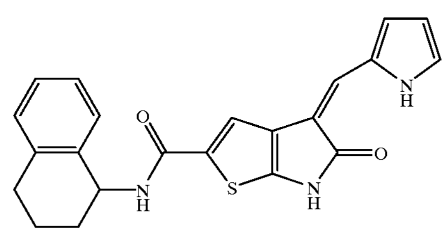 | 390 |
| 34 | (Z)-N-Cyclooctyl-5,6-dihydro-5-oxo-4-[(1H-pyrrol-2-yl)methylene]-4H-thieno[2,3-b]pyrrole-2-carboxamide | 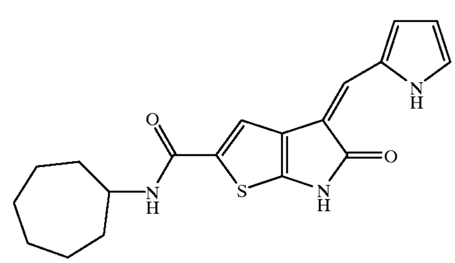 | 370 |

TABLE 3-continued

| Example | Name | Structure | MS (ES) |
|---|---|---|---|
| 35 | (Z)-N-(2-Furfuryl)-5,6-dihydro-5-oxo-4-[(1H-pyrrol-2-yl)methylene]-4H-thieno[2,3-b]pyrrole-2-carboxamide | 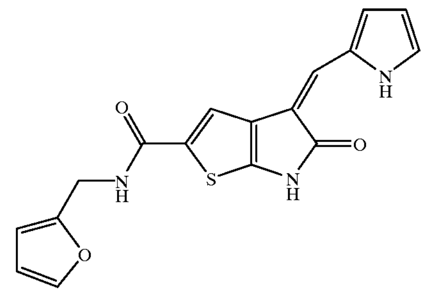 | 340 |
| 36 | (Z)-5,6-Dihydro-N-(tetrahydro-2(RS)-furfuryl)-5-oxo-4-[(1H-pyrrol-2-yl)methylene]-4H-thieno[2,3-b]pyrrole-2-carboxamide | 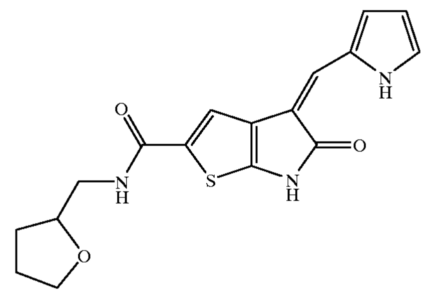 | 344 |
| 37 | (Z)-5,6-Dihydro-N-(2-hydroxy-1,1-dimethyl-ethyl)-5-oxo-4-[(1H-pyrrol-2-yl)methylene]-4H-thieno[2,3-b]pyrrole-2-carboxamide | 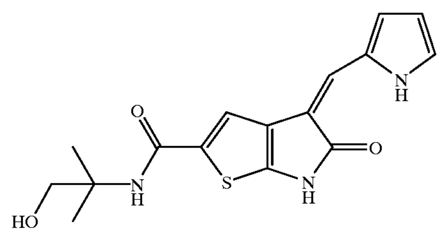 | 332 |
| 38 | (Z)-5,6-Dihydro-N-(2-hydroxy-1(R)-phenyl-ethyl)-5-oxo-4-[(1H-pyrrol-2-yl)methylene]-4H-thieno[2,3-b]pyrrole-2-carboxamide | 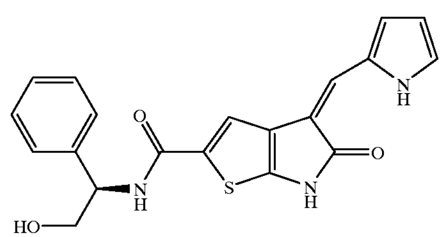 | 380 |
| 39 | (Z)-5,6-Dihydro-N-(1(RS),2-diphenylethyl)-5-oxo-4-[(1H-pyrrol-2-yl)methylene]-4H-thieno[2,3-b]pyrrole-2-carboxamide | 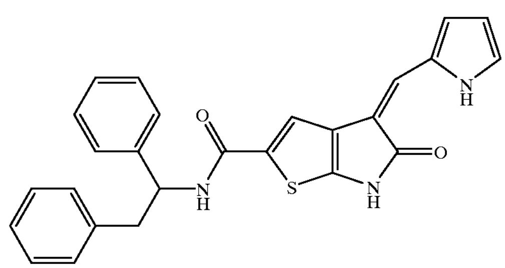 | 440 |

TABLE 3-continued

| Example | Name | Structure | MS (ES) |
|---|---|---|---|
| 40 | (Z)-5,6-Dihydro-N-(2,2-dimethyl-1(RS)-methyl-propyl)-5-oxo-4-[(1H-pyrrol-2-yl)methylene]-4H-thieno[2,3-b]pyrrole-2-carboxamide | 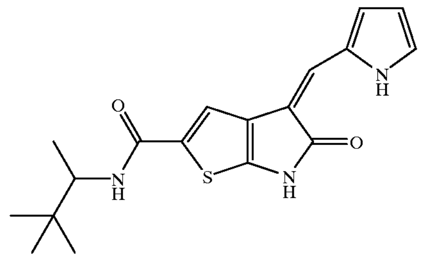 | 344 |
| 41 | (Z)-5,6-Dihydro-N-(2-methylpropyl)-5-oxo-4-[(1H-pyrrol-2-yl)-methylene]-4H-thieno-[2,3-b]pyrrole-2-carboxamide | 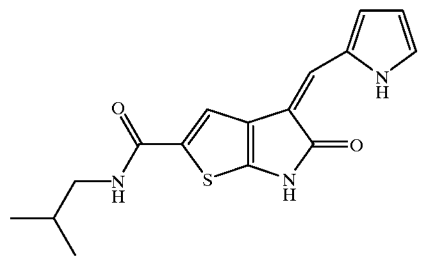 | 316 |
| 42 | (Z)-5,6-Dihydro-N-(2-methoxyethyl)-5-oxo-4-[(1H-pyrrol-2-yl)-methylene]-4H-thieno[2,3-b]pyrrole-2-carboxamide | 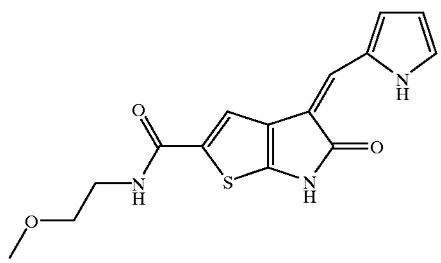 | 318 |
| 43 | (Z)-5,6-Dihydro-N-[2-(2-hydroxyethoxy)ethyl]-5-oxo-4-[(1H-pyrrol-2-yl)methylene]-4H-thieno[2,3-b]pyrrole-2-carboxamide | 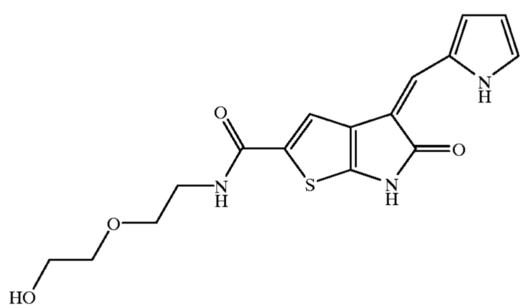 | 348 |
| 44 | (Z)-5,6-Dihydro-N-(5-hydroxypentyl)-5-oxo-4-[(1H-pyrrol-2-yl)-methylene]-4H-thieno-[2,3-b]pyrrole-2-carboxamide | 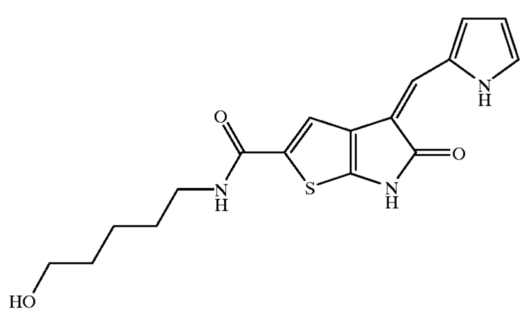 | 346 |

TABLE 3-continued

| Example | Name | Structure | MS (ES) |
|---|---|---|---|
| 45 | (Z)-5,6-Dihydro-5-oxo-4-[(1H-pyrrol-2-yl)methylene]-N-(4-sulfamoylbenzyl)-4H-thieno[2,3-b]pyrrole-2-carboxamide | 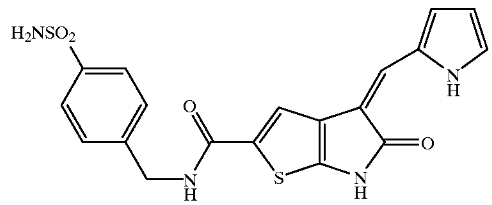 | 429 |
| 46 | (Z)-5,6-Dihydro-N-(tetrahydro-1,1-dioxo-3(RS)-thienyl)-5-oxo-4-[(1H-pyrrol-2-yl)methylene]-4H-thieno[2,3-b]pyrrole-2-carboxamide | 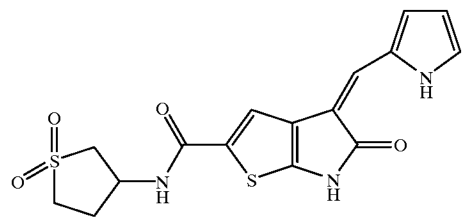 | 378 |
| 47 | (Z)-N-[2-(N-Ethyl-N-m-tolylamino)ethyl]-5,6-dihydro-5-oxo-4-[(1H-pyrrol-2-yl)methylene]-4H-thieno[2,3-b]pyrrole-2-carboxamide | 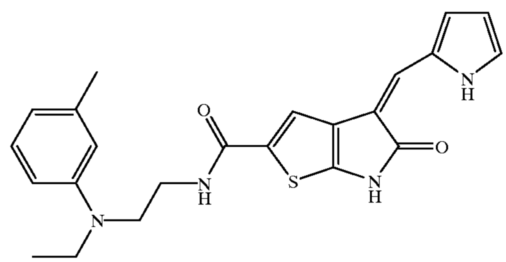 | 421 |
| 48 | (Z)-5,6-Dihydro-5-oxo-4-[(1H-pyrrol-2-yl)-methylene]-N-[2-(2-thienyl)ethyl]-4H-thieno[2,3-b]pyrrole-2-carboxamide | 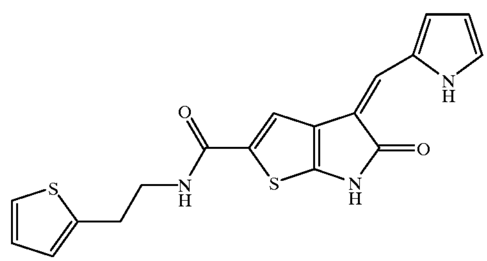 | 370 |
| 49 | (Z)-5,6-Dihydro-5-oxo-N-(2-phenoxyethyl)-4-[(1H-pyrrol-2-yl)methylene]-4H-thieno[2,3-b]pyrrole-2-carboxamide | 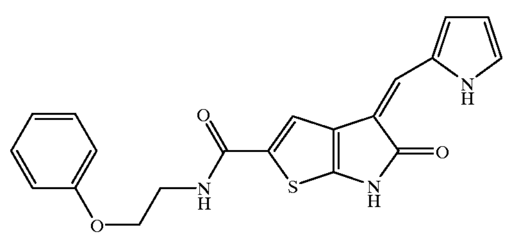 | 380 |
| 50 | (Z)-5,6-Dihydro-N-[2-(3-indolyl)ethyl]-5-oxo-4-[(1H-pyrrol-2-yl)-methylene]-4H-thieno-[2,3-b]pyrrole-2-carboxamide | 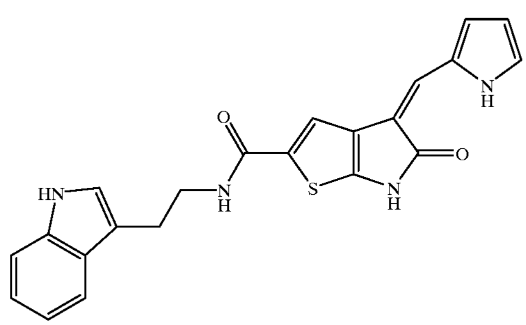 | 403 |

TABLE 3-continued

| Example | Name | Structure | MS (ES) |
|---|---|---|---|
| 51 | (Z)-5-Oxo-4-(1H-pyrrol-2-ylmethylene)-5,6-dihydro-4H-thieno[2,3-b]pyrrole-2-carboxylic acid (3-morpholin-4-yl-propyl)-amide | 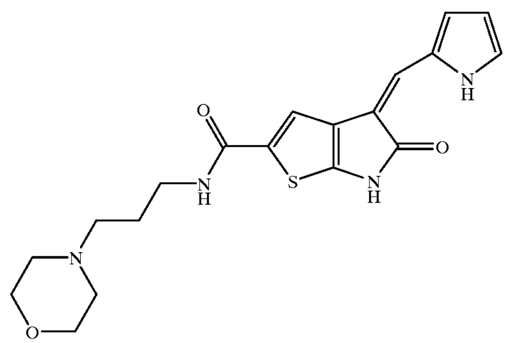 | 387 |
| 52 | (Z)-5-Oxo-4-(1H-pyrrol-2-ylmethylene)-5,6-dihydro-4H-thieno[2,3-b]pyrrole-2-carboxylic acid (2-hydroxy-ethyl)-amide | 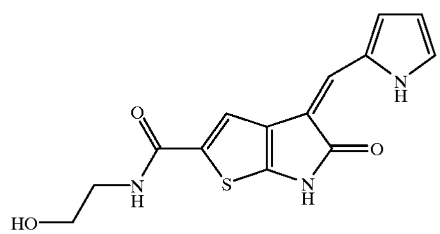 | 304 |
| 53 | (Z)-5-Oxo-4-(1H-pyrrol-2-ylmethylene)-5,6-dihydro-4H-thieno[2,3-b]pyrrole-2-carboxylic acid (2-acetylamino-ethyl)-amide | 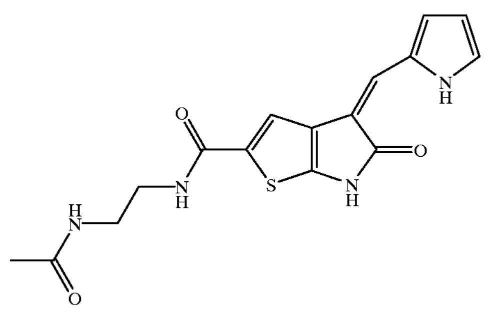 | 345 |
| 54 | (Z)-5-Oxo-4-(1H-pyrrol-2-ylmethylene)-5,6-dihydro-4H-thieno[2,3-b]pyrrole-2-carboxylic acid (2-carbamoyl-ethyl)-amide | 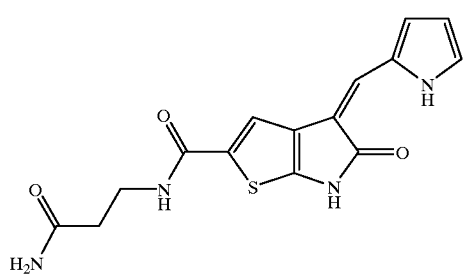 | 331 |
| 55 | (Z)-5-Oxo-4-(1H-pyrrol-2-ylmethylene)-5,6-dihydro-4H-thieno[2,3-b]pyrrole-2-carboxylic acid (pyridin-4-ylmethyl)-amide | 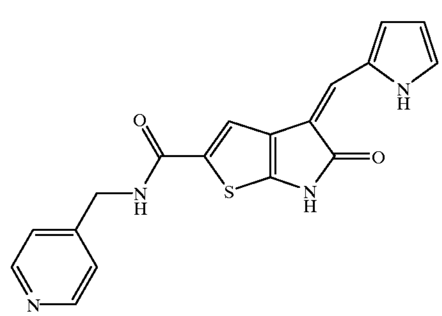 | 351 |

TABLE 3-continued

| Example | Name | Structure | MS (ES) |
|---|---|---|---|
| 56 | (Z)-5-Oxo-4-(1H-pyrrol-2-ylmethylene)-5,6-dihydro-4H-thieno[2,3-b]pyrrole-2-carboxylic acid (2-pyridin-2-yl-ethyl)-amide | 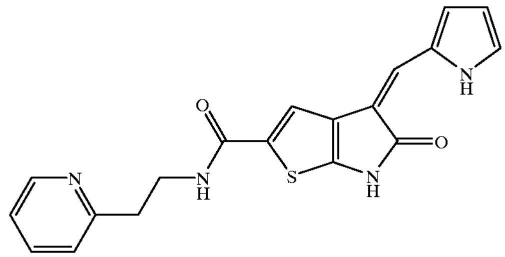 | 365 |
| 57 | (Z)-5-Oxo-4-(1H-pyrrol-2-ylmethylene)-5,6-dihydro-4H-thieno[2,3-b]pyrrole-2-carboxylic acid (pyridin-2-ylmethyl)-amide | 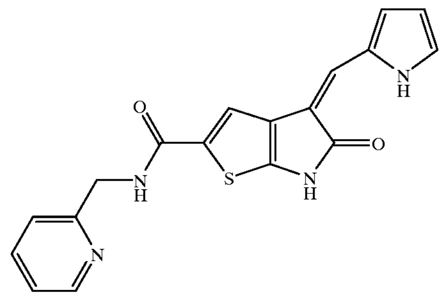 | 351 |
| 58 | (Z)-5-Oxo-4-(1H-pyrrol-2-ylmethylene)-5,6-dihydro-4H-thieno[2,3-b]pyrrole-2-carboxylic acid (2-pyrrolidin-1-yl-ethyl)-amide | 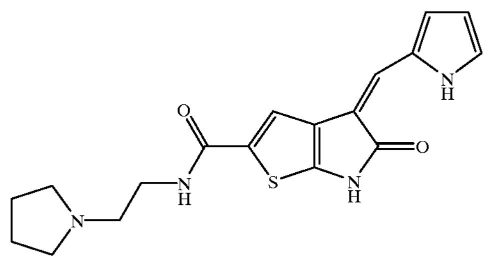 | 357 |
| 59 | (Z)-5-Oxo-4-(1H-pyrrol-2-ylmethylene)-5,6-dihydro-4H-thieno[2,3-b]pyrrole-2-carboxylic acid (2-phenyl-butyl)-amide | 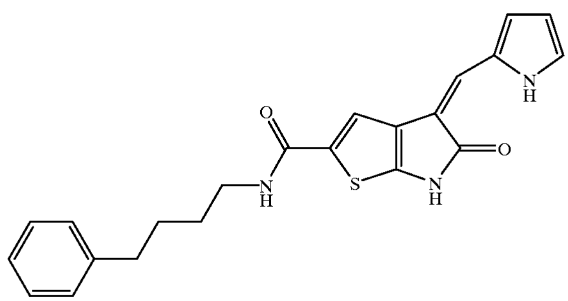 | 392 |
| 60 | (Z)-5-Oxo-4-(1H-pyrrol-2-ylmethylene)-5,6-dihydro-4H-thieno[2,3-b]pyrrole-2-carboxylic acid (6-chloro-1H-benzimidazol-2-ylmethyl)-amide | 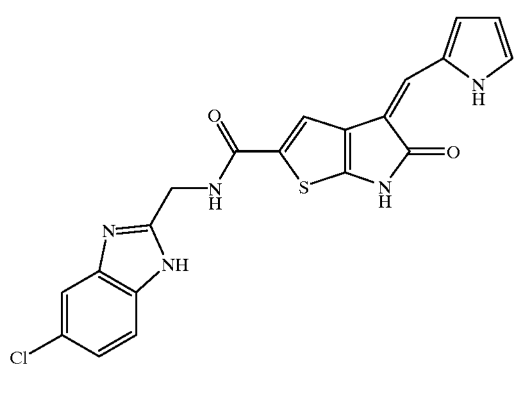 | 424 |

TABLE 3-continued

| Example | Name | Structure | MS (ES) |
|---|---|---|---|
| 61 | (Z)-5-Oxo-4-(1H-pyrrol-2-ylmethylene)-5,6-dihydro-4H-thieno[2,3-b]pyrrole-2-carboxylic acid [2-(5-chloro-1H-benzimidazol-2-yl)-ethyl]-amide | 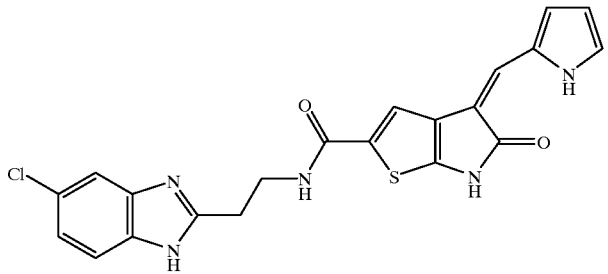 | 438 |
| 62 | (Z)-5-Oxo-4-(1H-pyrrol-2-ylmethylene)-5,6-dihydro-4H-thieno[2,3-b]pyrrole-2-carboxylic acid (6-methoxy-1H-benzimidazol-2-ylmethyl)-amide | 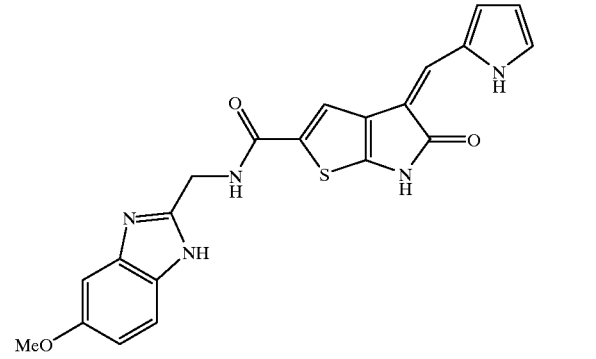 | 420 |
| 63 | (Z)-5-Oxo-4-(1H-pyrrol-2-ylmethylene)-5,6-dihydro-4H-thieno[2,3-b]pyrrole-2-carboxylic acid (1H-benzimidazol-2-ylmethyl)-amide | 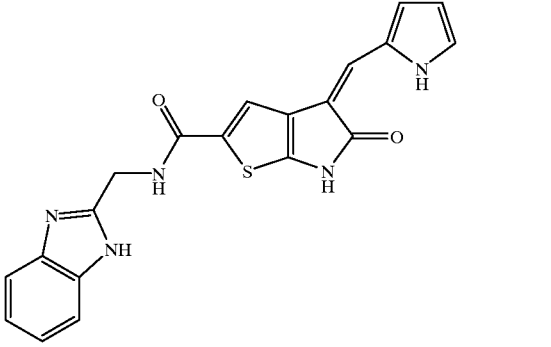 | 390 |
| 64 | (Z)-4-(3-Methoxy-1H-pyrrol-2-ylmethylene)-5,6-dihydro-4H-thieno[2,3-b]pyrrole-2-carboxylic acid (6-chloro-1H-benzimidazol-2-ylmethyl)-amide | 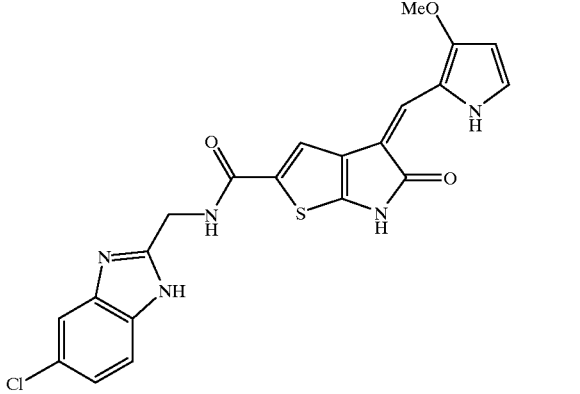 | 454 |

Example 65 tert-Butyl (Z)-5,6-dihydro-4-[(3-methoxy-1H-pyrrol-2-yl)methylene]-5-oxo-4H-thieno[2,3-b]pyrrole-2-carboxylate tert-Butyl 5,6-dihydro-5-oxo-4H-thieno[2,3-b]pyrrole-2-carboxylate (915 mg, 3.8 mmol) was dissolved in a solution of 1% piperidine in 2-propanol (10 ml). 3-Methoxypyrrole-2-carboxaldehyde (3.8 mmol, 480 mg) was added in one portion and the mixture heated at 75° C. for 1 hour. The reaction mixture was poured into an ice/water mixture (15 ml) and the precipitated solid was collected by filtration and washed with water to give 530 mg of tert-butyl (Z)-5,6-dihydro-4-[(3-methoxy-1H-pyrrol-2-yl)methylene]-5-oxo-4H-thieno [2,3-b]pyrrole-2-carboxylate as a red solid. MS(ES): m/e 347 [M+H].

Example 66

(Z)-5,6-Dihydro-4-[(3-methoxy-1H-pyrrol-2-yl) methylene]-5-oxo-4H-thieno[2,3-b]pyrrole-2-carboxylic acid tert-Butyl (Z)-5,6-dihydro-4-[(3-methoxy-1H-pyrrol-2-yl)methylene]-5-oxo-4H-thieno[2,3-b]pyrrole-2-carboxylate (0.5 g, 1.45 mmol) was dissolved in dichloromethane (8 ml), cooled to 0° C., treated with trifluoroacetic acid (2 ml) and stirred for 3 hours warming to room temperature. The reaction mixture was evaporated to dryness and triturated with diethyl ether to give 300 mg of (Z)-5,6-dihydro-4-[(3-methoxy-1H-pyrrol-2-yl)methylene]-5-oxo-4H-thieno[2,3-b]pyrrole-2-carboxylic acid as a red solid. MS(ES): m/e 291 [M+H].

Example 67

(Z)-5,6-Dihydro-4-[(3-methoxy-1H-pyrrol-2-yl) methylene]-5-oxo-4H-thieno[2,3-b]2pyrrole-2-carboxamide

5,6-Dihydro-5-oxo-4H-thieno[2,3-b]pyrrole-2-carboxamide (30 mg, 0.17 mmol) was dissolved in a solution of 1% piperidine in 2-propanol (2 ml). Pyrrole-2-carboxaldehyde (0.19 mmol, 23 mg) was added in one portion and the mixture heated at 75° C. for 1 hour. The reaction mixture was poured into an ice/water mixture (2 ml) and the precipitated solid was collected by filtration and washed with water to give 22 mg of (Z)-5,6-dihydro-4-[(3-methoxy-1H-pyrrol-2-yl)methylene]-5-oxo-4H-thieno[2,3-b]pyrrole-2-carboxamide as a red/brown solid. MS(ES): m/e 247 [M+H].

Example 68

(Z)-5,6-Dihydro-4-[(5-methyl-3H-imidazol-4yl) methylene]-5-oxo-4H-thieno[2,3-b]pyrrole-2-carboxamide

5,6-Dihydro-5-oxo-4H-thieno[2,3-b]pyrrole-2-carboxamide (30 mg, 0.17 mmol) was dissolved in a solution of 1% piperidine in 2-propanol (2 ml). 4-Methyl-5-imidazole carboxaldehyde (0.18 mmol, 15 mg) was added in one portion and the mixture heated at 75° C. for 1 hour. The reaction mixture was poured into an ice/water mixture (2 ml) and the precipitated solid was collected by filtration and washed with water to give 22 mg of (Z)-5,6-dihydro-4-[(3-methoxy-1H-pyrrol-2-yl)methylene]-5-oxo-4H-thieno[2,3-b]pyrrole-2-carboxamide as a yellow/brown solid. MS(ES): m/e 275 [M+H].

Example 69

(Z)-5,6-Dihydro-5-oxo-4-[(3-phenyl-1H-pyrazol-4-yl)methylene]-4H-thieno[2,3-b]pyrrole-2-carboxamide

5,6-Dihydro-5-oxo-4H-thieno[2,3-b]pyrrole-2-carboxamide (30 mg, 0.17 mmol) was dissolved in a solution of 1% piperidine in 2-propanol (2 ml). 3-Phenyl-1H-pyrazole-4-carboxaldehyde (0.18 mmol, 31 mg) was added in one portion and the mixture heated at 75° C. for 1 hour. The reaction mixture was poured into an ice/water mixture (2 ml) and the precipitated solid was collected by filtration and washed with water to give 26 mg of (Z)-5,6-dihydro-5-oxo-4-[(3-phenyl-1H-pyrazol-4-yl)methylene]-4H-thieno [2,3-b]pyrrole-2-carboxamide as a yellow/brown solid. MS(ES): m/e 337 [M+H].

Example 70

(Z)-5,6-Dihydro-5-oxo-4-[[3-(4-methoxyphenyl)-1H-pyrazol-4-yl]methylene]-4H-thieno [2,3-b] pyrrole-2-carboxamide

5,6-Dihydro-5-oxo-4H-thieno[2,3-b]pyrrole-2-carboxamide (25 mg, 0.14 mmol) was dissolved in a solution of 1% piperidine in 2-propanol (2 ml). 3-(4-Methoxyphenyl)-1H-pyrazole-4-carboxaldehyde (0.15 mmol, 28 mg) was added in one portion and the mixture heated at 75° C. for 1 hour. The reaction mixture was poured into an ice/water mixture (2 ml) and the precipitated solid was collected by filtration and washed with water to give 27 mg of (Z)-5,6-dihydro-5-oxo-4-[[3-(4-methoxyphenyl)-1H-pyrazol-4-yl]methylene]-4H-thieno [2,3-b]pyrrole-2-carboxamide as a brown solid. MS(ES): m/e 367 [M+H].

Example 71

(Z)-5-Oxo-4-[1H-pyrrol-2-ylmethylene]-5,6-dihydro-4H-thieno[2,3-b]pyrrole-2-carboxylic acid (tetrahydro-pyran-2-yloxy)-amide

A solution of (Z)-5,6-dihydro-5-oxo-4-[(1H-pyrrol-2-yl) methylene]-4H-thieno[2,3-b]pyrrole-2-carboxylic acid (250 mg, 0.95 mmol), 1-hydroxybenzotriazole (1.1 mmol, 150 mg), 1-(tetrahydro-pyran-2-yloxy) amine (1.25 mmol, 146 mg), 1-(3-dimethoxyaminopropyl)-3-ethylcarbodiimide hydrochloride (1.1 mmol, 208 mg) and diisopropylethylamine (1.1 mmol, 190 mg) in dimethylformamide (4 ml) was stirred at room temperature for 3 hours then diluted with ethyl acetate and washed with 2M hydrochloric acid, saturated sodium bicarbonate and water. The resulting solution was dried over magnesium sulfate and evaporated to dryness. The residue was triturated with water/isopropyl alcohol to give 90 mg of (Z)-5-Oxo-4-[1H-pyrrol-2-ylmethylene]-5,6-dihydro-4H-thieno[2,3-b]pyrrole-2-carboxylic acid (tetrahydro-pyran-2-yloxy)-amide as a brown solid. MS(ES): m/e 360 [M+H].

Example 72

(Z)-5-Oxo-4-[1H-pyrrol-2-ylmethylene]-5,6-dihydro-4H-thieno [23-b]pyrrole-2-carboxylic acid hydroxamide

(Z)-5-Oxo-4-[1H-pyrrol-2-ylmethylene]-5,6-dihydro-4H-thieno[2,3-b]pyrrole-2-carboxylic acid (tetrahydro-pyran-2-yloxy)-amide (65 mg, 0.18 mmol) was dissolved in methanol (2 ml). 4-Toluene sulfonic acid (0.09 mmol, 15 mg) was added in one portion and the solution stirred at room temperature for 2 hours. The solvent was evaporated and the residue triturated with diethyl ether to give 10 mg of (Z)-5-Oxo-4-[1H-pyrrol-2-ylmethylene]-5,6-dihydro-4H-thieno[2,3-b]pyrrole-2-carboxylic acid hydroxamide as a brown solid. MS(ES): m/e 276 [M+H].

Example 73

(Z)-2-Hydroxymethyl-4-(1H-pyrrol-2-ylmethylene)-4,6-dihydro-thieno[2,3-b]pyrrol-5-one tert-Butyl 5,6-Dihydro-5-oxo-4H-thieno[2,3-b]pyrrole-2-carboxylate (300 mg, 1 mmol) was dissolved in toluene (25 ml). Diisobutylaluminium hydride (1.5 mmol, 1.5 ml of a 1 M solution in toluene) was added dropwise and the reaction mixture stirred at room temperature for 2 hours. Methanol (1 ml) was added and then diluted with ethyl acetate and washed with 2M hydrochloric acid, saturated sodium bicarbonate and water. The resulting solution was dried over magnesium sulfate and evaporated to dryness to give 70 mg of (Z)-2-hydroxymethyl-4-(1H-pyrrol-2-ylmethylene)-4,6-dihydro-thieno[2,3-b]pyrrol-5-one as a red solid.

MS(ES): m/e 247 [M+H].

Example 74

(Z)-2-Methyl-4-(1H-pyrrol-2-ylmethylene)-4,6-dihydro-thieno[2,3-b]pyrrol-5-one tert-Butyl 5,6-Dihydro-5-oxo-4H-thieno[2,3-b]pyrrole-2-carboxylate (300 mg, 1 mmol) was dissolved in dichloromethane (40 ml). Diisobutylaluminium hydride (2 mmol, 2 ml of a 1 M solution in dichloromethane) was added dropwise and the reaction mixture stirred at room temperature for 2 hours then diluted with ethyl acetate and washed with saturated sodium bicarbonate, saturated brine solution and water. The resulting solution was dried over magnesium sulfate and evaporated to dryness and chromatographed on silica gel using hexane/ethyl acetate (5:1) as eluent to give 10 mg of (Z)-2-methyl-4-(1H-pyrrol-2-ylmethylene)-4,6-dihydro-thieno[2,3-b]pyrrol-5-one as a red solid. MS(ES): m/e 231 [M+H].

Example 75

(Z)-3-[5-Oxo-4-(1H-pyrrol-2-ylmethylene)-5,6-dihydro-4H-thieno[2,3-b]pyrrol-2-yl]-acrylic acid ethyl ester 3-(5-Oxo-5,6-dihydro-4H-thieno[2,3-b]pyrrol-2-yl)-acrylic acid ethyl ester (30 mg, 0.13 mmol) was dissolved in a solution of 1% piperidine in 2-propanol (1 ml). Pyrrole-2-carboxaldehyde (0.15 mmol, 14 mg) was added in one portion and the mixture heated at 75° C. for 30 minutes. The reaction mixture was poured into an ice/water mixture (4 ml) and the precipitated solid was collected by filtration and washed with water to give 10 mg of (Z)-3-[5-Oxo-4-(1H-pyrrol-2-ylmethylene)-5,6-dihydro-4H-thieno[2,3-b]pyrrol-2-yl]-acrylic acid ethyl ester as a red solid. MS(ES): mle 315 [M+H].

The starting material was prepared as follows:

Preparation of 3-(5-Oxo-5,6-dihydro-4H-thieno[2,3-b]pyrrol-2-yl)-acrylic acid ethyl ester i) A mixture of 5-nitrothiophene-2-carboxaldehyde (10 g, 64 mmol), hydroxylamine hydrochloride (9.4 g, 130 mmol) and sodium hydroxide (4.34 g, 107 mmol) in ethanol/water (150 ml, 2:1) was heated to reflux for 2 hours, then diluted with dichloromethane and washed with water. The organic layer was dried over magnesium sulfate and evaporated to dryness to give 8.8 g of 5-nitro-2-thiophene-carboxaldehyde oxime as a tan solid. $^1$H NMR (400 MHz, DMSO-d$_6$) δ: 7.54 (1H, d), 8.13 (1H, s), 8.16 (1H, d), 13.14 (1H, s).

ii) Potassium tertiary-butoxide (960 mg, 8.6 mmol) was dissolved in N,N-dimethylformamide (10 ml) and the solution cooled to −30° C. A solution of 5-nitro-2-thiophenecarboxaldehyde oxime (400 mg, 2.86 mmol) and ethyl chloroacetate (356 mg, 2.86 mmol) was added dropwise in dry N,N-dimethylformamide (5 ml) over 5 minutes. The reaction mixture was stirred at −30° C. for 30 minutes then quenched with 2M HCl (50 ml), diluted with ethyl acetate, washed with water, dried over magnesium sulfate and evaporated to dryness. The residue was chromatographed on silica gel using hexane/diethyl ether (1:2) as eluent to give 200 mg of ethyl-5-[(hydroxyimino)methyl]-2-nitro-3-thiopheneacetate as a tan solid. MS(ES): m/e 227 [M+H].

ii) A mixture of ethyl-5-[(hydroxyimino)methyl]-2-nitro-3-thiopheneacetate (1 g, 4.43 mmol) in aqueous formaldehyde (37%, 30 ml) and conc. sulfuric acid (0.1 ml) was refluxed for 30 minutes. The reaction mixture was cooled to room temperature then diluted with water and extracted with ethyl acetate. The organic phase was washed with saturated sodium hydrogen carbonate and saturated brine solution, dried over magnesium sulfate and evaporated to dryness and then chromatographed on silica gel using hexane/ethyl acetate (2:1) as eluent to give 500 mg of ethyl-5-nitrothiophene-4-acetate-2-carboxaldehyde. $^1$H NMR (400 MHz, CDCl$_3$) δ: 1.32 (3H, t), 4.25 (2H, q), 7.71 (1H, s), 9.96 (1H, s).

iv) Ethy-5-nitrothiophene-4-acetate-2-carboxaldehyde (350 mg, 1.44 mmol) was dissolved in dichloromethane, treated with (carbomethoxymethylene)-triphenylphosphorane (522 mg, 1.5 mmol) and heated to reflux for 1 hour. The reaction mixture was evaporated to dryness and then chromatographed on silica gel using hexanemdiethyl ether (1:1) as eluent to give 250 mg of ethyl-4-[(ethoxycarbonyl)methyl]-5-nitro-2-thiopheneacrylate. MS(ES): m/e 314 [M+H].

v) Ethyl-4-[(ethoxycarbonyl)methyl]-5-nitro-2-thiopheneacrylate (230 mg, 0.74 mmol) was dissolved in aqueous dioxan (6 ml, 5:1 dioxan/water) and treated with reduced iron powder (0.4 g, 7.2 mmol) and iron sulfate heptahydrate (50 mg, 0.18 mmol). The reaction mixture was refluxed for 1 hour then filtered through celite and washed through with diethyl ether. The combined organics were then washed with saturated sodium hydrogen carbonate, saturated sodium chloride, dried over magnesium sulfate and evaporated to dryness. The residue was chromatographed on silica gel using hexane/ethyl acetate (2:1) as eluent to give 150 mg 3-(5-amino-4-ethoxycarbonylmethyl-thiophen-2-yl)-acrylic acid ethyl ester. MS(ES): m/e 284 [M+H].

vi) Ethyl-4-[(ethoxycarbonyl)methyl]-5-amino-2-thiopheneacrylate (150 mg, 0.53 mmol) was dissolved in dichloromethane (20 ml), treated at room temperature with trimethyaluminium (2M in heptane, 1 ml, 2 mmol) and stirred for 1 hour. The reaction was quenched with water, diluted with ethyl acetate, washed with saturated brine solution and dried over magnesium sulfate. The organic phase was evaporated to dryness and the residue chromatographed on silica gel using hexane/ethyl acetate (2:1) as eluent to give 35 mg of 3-(5-oxo-5,6-dihydro-4H-thieno[2,3-b]pyrrol-2-yl)-acrylic acid ethyl ester as a tan colored solid.

MS(ES): m/e 238 [M+H].

Example 76

(Z)-2-Acetyl-4,6-dihydro-4-[(1H-pyrrol-2-yl)methylene]thieno[2,3-b]pyrrol-5-one

2-Acetyl-4,6-dihydro-4-thieno[2,3-b]pyrrol-5-one (16 mg, 0.08 mmol) was dissolved in a solution of 1% piperidine in 2-propanol (1 ml). Pyrrole-2-carboxaldehyde (0.16 mmol, 17 mg) was added in one portion and the mixture heated at 75° C. for 1 hour. The reaction mixture was poured into an ice/water mixture (3 ml) and the precipitated solid was collected by filtration and washed with water to give 7 mg of (Z)-2-Acetyl-4,6-dihydro-4-[(1H-pyrrol-2-yl)methylene]thieno[2,3-b]pyrrol-5-one as a red solid. MS(ES): m/e 259 [M+H].

The starting material was prepared as follows:

4,6-Dihydro-5H-thieno[2,3-b]pyrrol-5-one (70 mg, 0.5 mmol) was dissolved in boron trifluoride diethyletherate (4 ml) and treated with acetyl chloride (1.5 mmol, 0.11 ml) at room temperature. The reaction mixture was then heated to reflux for 3 hours, quenched with water, diluted with ethyl acetate and washed with 2M HCl solution. The organic phase was dried over magnesium sulfate, evaporated to dryness and the residue chromatographed on silica gel using hexane/ethyl acetate (1:1) as eluent to give 20 mg of 2-acetyl-4,6-dihydro-4-thieno[2,3-b]pyrrol-5-one as a brown solid. MS(ES): m/e 182 [M+H].

Example 77

Tablets containing the following ingredients maybe produced in a conventional manner:

| Ingredient | Per tablet |
| --- | --- |
| Thienopyrrolidinone derivative of formula I | 10.0 mg |
| Lactose | 135.0 mg |
| Microcrystalline cellulose | 50.0 mg |
| Talc | 4.0 mg |
| Magnesium stearate | 1.0 mg |
| Total weight | 200.0 mg |

Example 78

Capsules containing the following ingredients may be produced in a conventional manner:

| Ingredient | Per capsule |
| --- | --- |
| Thienopyrrolidinone derivative of formula I | 10.0 mg |
| Lactose | 155.0 mg |
| Pregelatinized starch | 30.0 mg |
| Talc | 5.0 mg |
| Capsule fill weight | 200.0 mg |

What is claimed is:
1. A compound of formula

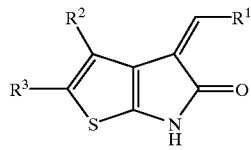

or a pharmaceutically acceptable salt thereof, wherein $R^1$ represents a 5- or 6-membered monocyclic aromatic ring containing one or more hetero atoms independently selected from N, S and O, the remaining atoms being carbon, said 5- or 6-membered aromatic ring not being fused or being fused to a benzene ring, said 5- or 6-membered monocyclic aromatic ring and said benzene ring each being unsubstituted or each being independently substituted with one or more substituents selected from the group consisting of lower alkyl, lower alkoxy, aryl, substituted aryl, aryl-lower alkyl, substituted aryl-lower alkyl, aryl-lower alkoxy, substituted aryl-lower alkoxy, halogen, haloalkyl, nitro, hydroxy, cyano, —C(O)$R^7$, —(CH$_2$)$_n$CO$_2$$R^8$, and —(CH$_2$)$_n$CONR$^7$R$^8$;

$R^7$ is selected from the group consisting of hydrogen, cycloalkyl, aryl, substituted aryl, heteroaryl, substituted heteroaryl, heterocyclyl, lower alkyl and lower alkyl that may be mono substituted by cycloalkyl, aryl, substituted aryl or heterocyclyl;

$R^8$ is selected from the group consisting of hydrogen, cycloalkyl, heterocyclyl, lower alkyl, and lower alkyl that may be mono substituted by cycloalkyl, aryl, substituted aryl, hydroxy, lower alkoxy, heteroaryl, substituted heteroaryl, heterocyclyl or hydroxy-loweralkoxy, or, when $R^7$ and $R^8$ are both attached to nitrogen, $R^7$ and $R^8$ together with the nitrogen atom to which they are attached represent a 5- or 6-membered heterocycle that does not contain or may contain an additional heteroatom selected from N, S and O and may or may not be substituted by lower alkyl, lower alkoxy or hydroxy-lower alkyl;

n is 0–3;

$R^2$ is H;

$R^3$ is selected from the group consisting of hydrogen, —COR$^4$, —CONR$^4$R$^5$, —CONHOR$^6$, cyano, halogen, —CO$_2$R$^5$, —SO$_2$NR$^4$R$^5$, —OR$^4$, lower alkyl, lower alkyl substituted independently by cycloalkyl, aryl, substituted aryl, heteroaryl, substituted heteroaryl, heterocyclyl, hydroxy, —CONR$^4$R$^5$ or —CO$_2$R$^5$, lower alkenyl, and lower alkenyl substituted independently by cycloalkyl, aryl, substituted aryl, heteroaryl, substituted heteroaryl, heterocyclyl, hydroxy, —CONR$^4$R$^5$ or —CO$_2$R$^5$;

$R^4$ is selected from the group consisting of hydrogen, cycloalkyl, aryl, substituted aryl, heteroaryl, substituted heteroaryl, heterocyclyl, lower alkyl and lower alkyl that may be mono substituted by cycloalkyl, aryl, substituted aryl or heterocyclyl;

$R^5$ is selected from the group consisting of hydrogen, cycloalkyl, aryl, substituted aryl, heteroaryl, substituted heteroaryl, heterocyclyl, lower alkyl, and lower alkyl substituted independently by —CONH$_2$, cycloalkyl, aryl, substituted aryl, aryloxy, substituted aryloxy, hydroxy, lower alkoxy, heteroaryl, substituted heteroaryl, heterocyclyl, hydroxy-loweralkoxy or —NR'R" wherein R' is hydrogen, lower alkyl, or lower alkyl substituted by aryl or substituted aryl and R" is —COCH$_3$, lower alkyl, aryl or substituted aryl; or alternatively, when R$^4$ and R$^5$ are both attached to nitrogen, R$^4$ and R$^5$ together with the nitrogen atom to which they are attached represent a 5- or 6-membered heterocycle that does not contain or may contain an additional heteroatom selected from N, S and O and may or may not be independently substituted at one or more carbon and/or N-atoms by lower alkyl, lower alkoxy or hydroxy-lower alkyl; and R$^6$ represents hydrogen or heterocyclyl.

2. The compound of claim 1, wherein in R$^1$ the monocyclic aromatic ring is selected from the group consisting of pyrrolyl, pyrazolyl, imidazolyl, 1,2,3-triazolyl, 1,2,4-triazolyl, tetrazolyl, thienyl and furanyl.

3. The compound of claim 1 wherein R$^1$ is a 5- or 6-membered monocyclic aromatic ring that is fused with benzimidazolyl or indolyl.

4. The compound of claim 2, wherein the monocyclic aromatic ring in R$^1$ is pyrrolyl.

5. The compound of claim 2, wherein the monocyclic aromatic ring in R$^1$ is pyrazolyl.

6. The compound of claim 1, wherein the 5- or 6-membered monocyclic aromatic ring in R$^1$ is unsubstituted.

7. The compound of claim 1 wherein the 5- or 6-membered monocyclic aromatic ring in R$^1$ is fused to an unsubstituted benzene.

8. The compound of claim 1 wherein the 5- or 6-membered monocyclic aromatic ring has from 1–4 hetero atoms.

9. The compound of claim 1, wherein the monocyclic and benz-fused rings of R$^1$ are each independently substituted at one or more positions with lower alkyl, lower alkoxy, aryl, substituted aryl or —(CH$_2$)$_n$CO$_2$R$^8$.

10. The compound of claim 9, wherein the monocyclic or benz-fused aromatic ring in R$^1$ is each of independently substituted by methyl, phenyl, 2-nitrophenyl, p-methoxyphenyl, methoxy, carbethoxy, carbethoxymethyl or carbethoxyethyl.

11. The compound of claim 10, wherein R$^1$ is 2-pyrrolyl or 1H-pyrazol-4-yl.

12. The compound of claim 1, wherein R$^3$ is selected from the group consisting of hydrogen, —COR$^4$, —CONR$^4$R$^5$, —CONHOR$^6$, cyano, —CO$_2$R$^5$, —SO$_2$NR$^4$R$^5$, lower alkyl, lower alkyl substituted by hydroxy, lower alkenyl, or lower alkenyl substituted by —CO$_2$R$^5$.

13. The compound of claim 12, wherein R$^3$ is hydrogen, —CONH$_2$ or cyano.

14. The compound of claim 12, wherein R$^6$ is hydrogen.

15. The compound of claim 12, wherein R$^4$ is methyl.

16. The compound of claim 12, wherein R$^5$ is hydrogen, methyl or tert-butyl.

17. The compound (Z)-4,6-Dihydro-4-[(1H-pyrrol-2-yl)methylene]thieno[2,3-b]pyrrol-5-one.

18. The compound (Z)-4,6-Dihydro-4-[(3-methoxy-1H-pyrrol-2-yl)methylene]thieno[2,3-b]pyrrol-5-one.

19. The compound (Z)-5,6-Dihydro-5-oxo-4-[(1H-pyrrol-2-yl)methylene]-4H-thieno[2,3-b]pyrrole-2-carboxamide.

20. The compound (Z)-5,6-Dihydro-5-oxo-4-[(1H-pyrrol-2-yl)methylene]-4H-thieno[2,3-b]pyrrole-2-carbonitrile.

21. A compound selected from the group consisting of:

(Z) -4,6-Dihydro-4-[(3-methyl-1H-pyrazol-4-yl)methylene]thieno[2,3-b]pyrrol-5-one;
(Z)-4,6-Dihydro-4-[(3-phenyl-1H-pyrazol-4-yl)methylene]thieno[2,3-b]pyrrol-5-one; and (Z)-4,6-Dihydro-4-[[3-(4-methoxyphenyl)-1H-pyrazol-4-yl]methylene]thieno [2,3-b]pyrrol-5-one.

22. A compound of formula

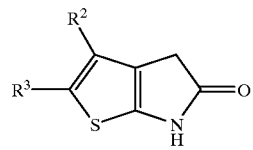

II wherein

R$^2$ is H;

R$^3$ is selected from the group consisting of hydrogen, —COR$^4$, —CONR$^4$R$^5$, —CONHOR$^6$, cyano, halogen, —CO$_2$R$^5$, —SO$_2$NR$^4$R$^5$, —OR$^4$, lower alkyl, lower alkyl substituted independently by cycloalkyl, aryl, substituted aryl, heteroaryl, substituted heteroaryl, heterocyclyl, hydroxy, —CONR$^4$R$^5$ or —CO$_2$R$^5$, lower alkenyl, and lower alkenyl substituted independently by cycloalkyl, aryl, substituted aryl, heteroaryl, substituted heteroaryl, heterocyclyl, hydroxy, —CONR$^4$R$^5$ or —CO$_2$R$^5$;

R$^4$ is selected from the group consisting of hydrogen, cycloalkyl, aryl, substituted aryl, heteroaryl, substituted heteroaryl, heterocyclyl, lower alkyl, and lower alkyl that may be mono substituted by cycloalkyl, aryl, substituted, aryl or heterocyclyl;

R$^5$ is selected from the group consisting of hydrogen, cycloalkyl, aryl, substituted aryl, heteroaryl, substituted heteroaryl, heterocyclyl, lower alkyl, and lower alkyl substituted independently by —CONH$_2$, cycloalkyl, aryl, substituted aryl, aryloxy, substituted aryloxy, hydroxy, lower alkoxy, heteroaryl, substituted heteroaryl, heterocyclyl, hydroxy-loweralkoxy or —NR'R" wherein R' is hydrogen, lower alkyl, or lower alkyl substituted by aryl or substituted aryl and R" is —COCH$_3$, lower alkyl, aryl or substituted aryl; or alternatively, when R$^4$ and R$^5$ are both attached to nitrogen, R$^4$ and R$^5$ together with the nitrogen atom to which they are attached represent a 5- or 6-membered heterocycle that does not contain or may contain an additional heteroatom selected from N, S and O and may or may not be independently substituted at one or more carbon and/or N-atoms by lower alkyl, lower alkoxy or hydroxy-lower alkyl; and R$^6$ represents hydrogen or heterocyclyl.

23. A pharmaceutical composition for the treatment of rheumatoid arthritis comprising an effective amount of a compound of formula I or a pharmaceutically acceptable salt thereof and a carrier.

24. A pharmaceutical composition for the treatment of Alzheimer's disease comprising an effective amount of a compound of formula I or a pharmaceutically acceptable salt thereof and a carrier.

25. A process for the manufacture of a compound of formula I comprising reacting a compound of formula

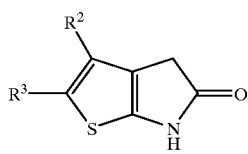

with an aldehyde of formula $R^1$—CHO  III, wherein

- $R^1$ represents a 5- or 6-membered monocyclic aromatic ring containing one or more hetero atoms independently selected from N, S and O, the remaining atoms being carbon, said 5- or 6-membered aromatic ring not being fused or being fused to a benzene ring, said 5- or 6-membered monocyclic aromatic ring and said benzene ring each being unsubstituted or each being independently substituted with one or more substituents selected from the group consisting of lower alkyl, lower alkoxy, aryl, substituted aryl, aryl-lower alkyl, substituted aryl-lower alkyl, aryl-lower alkoxy, substituted aryl-lower alkoxy, halogen, haloalkyl, nitro, hydroxy, cyano, —C(O)$R^7$, —(CH$_2$)$_n$CO$_2R^8$, and —(CH$_2$)$_n$CONR$^7R^8$;
- $R^7$ is selected from the group consisting of hydrogen, cycloalkyl, aryl, substituted aryl, heteroaryl, substituted heteroaryl, heterocyclyl, lower alkyl and lower alkyl that may be mono substituted by cycloalkyl, aryl, substituted aryl or heterocyclyl;
- $R^8$ is selected from the group consisting of hydrogen, cycloalkyl, heterocyclyl, lower alkyl, and lower alkyl that may be mono substituted by cycloalkyl, aryl, substituted aryl, hydroxy, lower alkoxy, heteroaryl, substituted heteroaryl, heterocyclyl or hydroxy-loweralkoxy, or, when $R^7$ and $R^8$ are both attached to nitrogen, $R^7$ and $R^8$ together with the nitrogen atom to which they are attached represent a 5- or 6-membered heterocycle that does not contain or may contain an additional heteroatom selected from N, S and O and may or may not be substituted by lower alkyl, lower alkoxy or hydroxy-lower alkyl;
- n is 0–3;
- $R^2$ is H;
- $R^3$ is selected from the group consisting of hydrogen, —COR$^4$, —CONR$^4R^5$, —CONHOR$^6$, cyano, halogen, —CO$_2R^5$, —SO$_2$NR$^4R^5$, —OR$^4$, lower alkyl, lower alkyl substituted independently by cycloalkyl, aryl, substituted aryl, heteroaryl, substituted heteroaryl, heterocyclyl, hydroxy, —CONR$^4R^5$ or —CO$_2R^5$, lower alkenyl, and lower alkenyl substituted independently by cycloalkyl, aryl, substituted aryl, heteroaryl, substituted heteroaryl, heterocyclyl, hydroxy, —CONR$^4R^5$ or —CO$_2R^5$;
- $R^4$ is selected from the group consisting of hydrogen, cycloalkyl, aryl, substituted aryl, heteroaryl, substituted heteroaryl, heterocyclyl, lower alkyl, and lower alkyl that may be mono substituted by cycloalkyl, aryl, substituted aryl or heterocyclyl;
- $R^5$ is selected from the group consisting of hydrogen, cycloalkyl, aryl, substituted aryl, heteroaryl, substituted heteroaryl, heterocyclyl, lower alkyl, lower alkyl substituted independently by —CONH$_2$, cycloalkyl, aryl, substituted aryl, aryloxy, substituted aryloxy, hydroxy, lower alkoxy, heteroaryl, substituted heteroaryl, heterocyclyl, hydroxy-loweralkoxy or —NR'R" wherein R' is hydrogen, lower alkyl, or lower alkyl substituted by aryl or substituted aryl and R" is —COCH$_3$, lower alkyl, aryl or substituted aryl;
- or alternatively, when $R^4$ and $R^5$ are both attached to nitrogen, $R^4$ and $R^5$ together with the nitrogen atom to which they are attached represent a 5- or 6-membered heterocycle that does not contain or may contain an additional heteroatom selected from N, S and O and may or may not be independently substituted at one or more carbon and/or N-atoms by lower alkyl, lower alkoxy or hydroxy-lower alkyl; and
- $R^6$ represents hydrogen or heterocyclyl.

26. A method of treating rheumatoid arthritis comprising administering to a patient in need of treatment an effective amount of a compound of formula I or a pharmaceutically acceptable salt thereof.

27. The method of claim 26 wherein the effective amount of a compound of formula I or a pharmaceutically acceptable salt thereof is from about 0.1 mg/kg/day to about 50 mg/kg/day.

28. The method of claim 27 wherein the effective amount of compound of formula I or a pharmaceutically acceptable salt thereof is from about 0.5 mg/kg/day to about 5 mg/kg/day.

29. A method of treating Alzheimer's disease comprising administering to a patient in need of treatment from about 0.5 mg/kg/day to about 5 mg/kg/day of a compound of formula I or a pharmaceutically acceptable salt thereof.

* * * * *